(12) United States Patent
Zargari et al.

(10) Patent No.: US 9,157,919 B2
(45) Date of Patent: Oct. 13, 2015

(54) METHOD FOR IDENTIFYING BIOLOGICALLY ACTIVE OLIGONUCLEOTIDES CAPABLE OF MODULATING THE IMMUNE SYSTEM

(75) Inventors: Arezou Zargari, Solna (SE); Nicolai Kouznetzov, Järfälla (SE); Charlotte Admyre, Vendelsö (SE); Petra Von Stein, Upplands Väsby (SE); Oliver Von Stein, Upplands Väsby (SE)

(73) Assignee: INDEX PHARMACEUTICALS AB, Stockholm (SE)

( * ) Notice: Subject to any disclaimer, the term of this patent is extended or adjusted under 35 U.S.C. 154(b) by 0 days.

(21) Appl. No.: 13/995,304

(22) PCT Filed: Dec. 20, 2011

(86) PCT No.: PCT/EP2011/073468
§ 371 (c)(1),
(2), (4) Date: Jun. 18, 2013

(87) PCT Pub. No.: WO2012/084996
PCT Pub. Date: Jun. 28, 2012

(65) Prior Publication Data
US 2013/0281519 A1      Oct. 24, 2013

(30) Foreign Application Priority Data

Dec. 21, 2010 (EP) .................................. 10196273
Dec. 21, 2010 (EP) .................................. 10196285
Dec. 21, 2010 (EP) .................................. 10196290

(51) Int. Cl.
*C07H 19/00* (2006.01)
*C12P 19/34* (2006.01)
*G01N 33/68* (2006.01)
*C12N 15/117* (2010.01)

(52) U.S. Cl.
CPC .......... *G01N 33/6869* (2013.01); *C12N 15/117* (2013.01); *G01N 33/6866* (2013.01); *C12N 2310/17* (2013.01); *C12N 2320/11* (2013.01)

(58) Field of Classification Search
None
See application file for complete search history.

(56) References Cited

FOREIGN PATENT DOCUMENTS

WO    WO 2008136748 A1 * 11/2008
WO    WO 2010053433 A1 *  5/2010

OTHER PUBLICATIONS

Abstract of WO 2005/116204 (full document is in Japanese), published in Dec. 2005, and a sequence search page.*
Abstract of WO 2002/18632 (full document is in German), published in Mar. 2002, and sequence search page.*

* cited by examiner

*Primary Examiner* — Tracy Vivlemore
*Assistant Examiner* — Kate Poliakova
(74) *Attorney, Agent, or Firm* — Birch, Stewart, Kolasch & Birch, LLP

(57) ABSTRACT

The present invention relates to methods of identifying oligonucleotides capable of modulating the immune system in a mammalian subject, comprising analysis of which tertiary structural type said oligonucleotide adopts, in phosphate-buffered saline solution. Further, the invention provides oligonucleotides identifiable by the methods of the invention and to their use in methods of treating diseases, such as inflammatory diseases, autoimmune diseases, infectious diseases, neurodegenerative diseases and cancer.

16 Claims, 13 Drawing Sheets

| standard component # | 1 | 2 | 3 | 4 | 5 | 6 | 7 | 8 |
|---|---|---|---|---|---|---|---|---|
| input (%) | 0.0 | 0.0 | 0.0 | 0.0 | 91.6 | 0.0 | 8.4 | 0.0 |

| standard component # | 1 | 2 | 3 | 4 | 5 | 6 | 7 | 8 |
|---|---|---|---|---|---|---|---|---|
| input (%) | 61.0 | 0.0 | 0.0 | 0.0 | 14.8 | 0.0 | 17.5 | 7.7 |

METHOD FOR IDENTIFYING BIOLOGICALLY ACTIVE OLIGONUCLEOTIDES CAPABLE OF MODULATING THE IMMUNE SYSTEM

FIELD OF THE INVENTION

The present invention refers to methods of identifying oligonucleotides that adopts a certain tertiary structure, and thereby are able to modulate the immune system, irrespective of primary structure. The present invention relates to methods of identifying oligonucleotides capable of modulating the immune system in a mammalian subject, comprising analysis of which tertiary structural type said oligonucleotide adopts, in physiologically relevant aqueous solution. Further, the invention provides oligonucleotides identifiable by the methods of the invention and to their use in methods of treating diseases, such as inflammatory diseases, autoimmune diseases, infectious diseases, neurodegenerative diseases and cancer.

BACKGROUND

DNA oligonucleotides (oligodeoxyribonucleotides, oligodeoxyribonucleic acids, ODNs, oligonucleotides) are short DNA-based synthetic polymers that can be synthesised and highly purified in significant quantities. The sequence of monomers (deoxyribonucleotides) in oligonucleotides is termed as the primary structure of DNA. The secondary structure of a nucleic acid molecule refers to the base-pairing interactions within a single molecule or set of interacting molecules. The tertiary structure of DNA is determined as its spatial organization (IUPAC). ODNs in physiologically relevant aqueous solutions are considered to be random-coiled single-stranded or in the tertiary structure of double-stranded DNA helix.

The double helix is the dominant tertiary structure for biological DNA that can be in one of three DNA conformations and are believed to be found in nature, A-DNA, B-DNA, and Z-DNA. The B-form described by Watson and Crick is believed to predominate in cells (Richmond T. J., et al. (2003) Nature 423 (6936): 145-150). However, several types of nucleic acid structures can be observed that are different from random or classical double-stranded helix forms. Among them are triplexes, quadruplexes and other nucleic acid structures (Soyfer, V. N and Potaman V. N. (1995) Triple-Helical Nucleic Acids. Springer Ver., New York, 360 pp; Burge S., et al. (2006) Nucleic Acids Research, 34, 19, 5402-5415).

Recently, it has been found that particular G-rich DNA sequences are capable of forming stable four-stranded structures known as G-quadruplexes (G-quartets) (Burge S., et al. (2006) Nucleic Acids Research, 34, 19, 5402-5415; Huppert, J. L. (2008) 37(7):1375-84; Neidle and Balasubramanian (2006) Quadruplex Nucleic Acids, RSC Publishing, Cambridge, UK, 302 pp). G-quartets arise from the association of four adjacent G-bases assembled into a cyclic conformation. These structures are stabilized by von Hoogsteen hydrogen bonding and by base stacking interactions (Skogen M., et al., (2006) BMC Neuroscience 7:65). G-quadruplexes have been shown to be relevant in biological processes as being important components of human telomeres, and playing a role in the regulation of transcription as well as translation (Patel et al., (2007) Nucleic Acids Res. 35(22):7429-55; Oganesian L, and Bryan T M (2007) Bioessays 29(2):155-65; Qin and Hurley (2008) Biochimie., 90 (8):1149-71; Siddiqui-Jain et al., (2002) Proc Natl Acad Sci USA. (2002) 3; 99(18):11593-8; Kumari et al., (2007) Nat Chem Biol. 2007, 3(4):218-21).

Parekh-Olmedo et al., ((2004) J Mol Neurosci. 24(2):257-67) showed that certain groups of ODNs can inhibit pathological protein aggregation in Huntington's disease. One of these groups was the G-rich oligonucleotides (GROs). G-quartet formation has also been implicated in the non-antisense antiproliferative effects of GROs. In several cases, the biological effects of oligonucleotides designed as antisense agents were found to be unrelated to inhibition of target protein expression, but instead were associated with the formation of G-quartet structures (Burgess et al., (1995) Proc. Natl. Acad. Sci. USA, 92, 4051-4055; Anselmet, A., et al., (2002) FEBS Lett., 510, 175-180; Benimetskaya, L., et al., (1997) Nucleic Acids Res., 25, 2648-2656; Saijo, Y et al., (1997) Jpn J. Cancer Res., 88, 26-33).

The molecular mechanisms of GRO action are not fully known. One of them appears to be related to the ability of oligonucleotides to bind to nucleolin (Bates, P. J., et al. (1999) J. Biol. Chem., 274, 26369-26377). Binding of nucleolin to other G-quartet-forming sequences such as telomeric DNA, immunoglobulin switch regions and ribosomal genes has also been reported (Dempsey, L. A., et al., (1999) J. Biol. Chem., 274, 1066-1071; Hanakahi, L. A. et al., (1999) J. Biol. Chem., 274, 15908-15912; Ishikawa, F. et al., (1999) Mol. Cell. Biol. 13, 4301-4310; Dickinson, L. A. and Kohwi-Shigematsu, T. (1995) Mol. Cell. Biol., 15, 456-465).

Treatment of tumour cells with G-rich oligonucleotides was found to inhibit cell cycle progression by specifically interfering with DNA replication, whereas GRO-treated normal skin cells exhibited minimal perturbation of the cell cycle (Xu X., et al., (2001) J. Biol. Chem. 276, 43221-43230). Further, Antisoma plc, developed G-quadruplex based AS-1411 that is the first oligodeoxyribonucleotide aptamer that reached clinical trials for the potential treatment of cancers, including acute myelogenous leukemia (AML) (Ireson C R and Kelland L R, (2006) Mol Cancer Ther. 5 (12):2957-62; Mongelard F. and Bouvet P., (2006) Curr Opin Mol Ther. 12(1): 107-14).

G-rich oligonucleotides can form a variety of possible quadruplex structures, depending on its thermodynamic and kinetic characteristics. Quadruplexes can be formed by one, two or four molecules of oligonucleotides, which are referred to as monomer, dimer and tetramer structures, respectively. (Dapic V., et al., (2003) Nucleic Acids Research 31 (8): 2097-2107).

Circular dichroism (CD) spectroscopy is commonly used to investigate the structure and conformation of nucleic acids (Baase and Johnson Jr. (1979) Nucleic Acids Res., 6(2): 797-814; Giraldo R. et al., (1994) Proc. Natl. Acad. Sci. USA 91: 7658-7662; Hardin C. C. et al., (1991) Biochemistry 30:4460-44721992, Hardin C. C. et al., (1992) Biochemistry 31: 833-841; Paramasivan S, et al. (2007) Methods 43: 324-331) where circular dichroism refers to the differential absorption of left and right circularly polarized light (P. Atkins and J. de Paula (2005) Elements of Physical Chemistry, 4th ed. Oxford University Press). Various DNA quadruplex structures have distinctive circular dichroism spectra (Dapic V, et al., (2003) Nucleic Acids Research 31 (8): 2097-2107) providing the possibility to use selected structures as set of standards or references to compare with CD spectra of oligonucleotides.

Various immunostimulatory oligodeoxyribonucleotides containing unmethylated deoxyribodinucleotide CpG motifs (CpG ODNs) that mimic prokaryotic DNA have been developed and characterised by several research groups. It has been established that recognition of CpG ODN requires Toll-like receptor 9 (TLR9) interaction. Cells that express TLR9, which include plasmacytoid dendritic cells (PDCs) and B cells, produce Th1-like proinflammatory cytokines, interferons, and chemokines in response to CpG ODNs. Several classes of CpG ODNs are described up to date as A-, B-, C-, D- and P-class CpG ODNs (Krieg A., 2002 and 2006), however, they all have been classified based on the primary structure (nucleotide sequence) of the oligonucleotides.

In recent years, there has been tremendous progress delineating the specific components of the immune system that contribute to various aspects of normal immunity and specific disease states. This has introduced the possibility to treat diseases with immunomodulating substances as protein therapeutics, including monoclonal antibodies and cytokines, which became mainstream treatments in a number of clinical settings.

Imbalances in the cytokine cascade can help the initiation and propagation of the immune driven inflammation. In several inflammatory diseases, including rheumatoid arthritis and inflammatory bowel disease, the proinflammatory cytokine TNF-α has been shown to play a central role in inflammatory reactions and has proven to be an especially attractive target for biological agents. Immunomodulatory cytokines considered of significance in the treatment of infectious diseases, malignancies and autoimmune diseases including interferon type I (IFN-α and IFN-β), IFN-γ and IL-10.

Interferons (IFNs) are cytokines that may be released in response to viruses, bacteria, parasites and tumor cells. Interferons possess immunoregulatory, antiviral and anti-cancer properties. They have been used to successfully treat a number of chronic inflammatory disorders including multiple sclerosis (Paolicelli, D et al., (2009) Targets & Therapy; 3, 369-76), chronic viral hepatitis (Hoofnagel J H and Seeff L B, (2006) N. Eng. J. Med., 355: 2444-51; Chevaliez S and Pawlotsky J M, (2009) Handbook of Experimental Pharmacology, Antiviral Strategies, 189: 203-41) and also in neoplastic diseases (Gill P S et al., (1995) N. Eng. J. Med., 332:1744-8). There are two main classes of IFNs: Type I IFNs (α,β,ε,ο,κ) are central in the host defense against pathogens such as viruses whereas type II IFN (γ) mainly contributes to the T-cell-mediated regulation of the immune responses.

IFN-α is produced by the cells of the immune system in response to the presence of a foreign antigen, inducing cell activation of macrophages and natural killer cells and enhancing antigen presentation. There are 13 subtypes of IFN-α, whereby the two subtypes IFN-α2a and IFN-α2b have been used therapeutically with similar results in hepatitis C (Wetzel T M et al., (2009) Hepatology, 49: 1847-58) and renal carcinoma (Coppin C et al., (2008) The Cochrane Collaboration, Targeted therapy for advanced renal cell carcinoma, 1-38). The side effects of recombinant IFN-α can, however, be significant with up to 68% of patients presenting with psychiatric symptoms, such as depression, irritability, and insomnia.

IFN-β is produced mainly in fibroblasts and plasmacytoid dendritic cells and has 30% nucleic acid homology to IFN-α and sharing similar antiviral activity. Clinically, it has been used in the treatment of MS because of its additional anti-inflammatory effect (Durelli L et al., (2009) Ann Neurol, 65: 499-509). Currently, recombinant IFN-β is used as a first-line treatment for relapsing-remitting form of the MS disease. Common adverse events from the recombinant IFN-β are depression, flu-like symptoms, and increase of liver enzyme levels. In addition, treatment results in the induction of anti-IFN-β neutralizing antibodies (NAbs) in some patients resulting in a lost effect of treatment (Soelberg Sorensen P et al., (2003) Lancet, Vol. 362: 1184-91; Soelberg Sorensen P et al., (2006) Neurology, 67: 1681-3). IFN-β was also used successfully as therapy in chronic inflammatory diseases as ulcerative colitis (Musch E et al., (2002) Aliment Pharmacol Ther, 3: 581-6).

IFN-γ is produced by leukocytes to induce macrophage activation and increase oxidative burst. Defects in IFN-γ and IFN-γ receptor genes have been associated with autoimmune diseases such as rheumatoid arthritis, type1 diabetes and multiple sclerosis (Chen J and Liu X, (2009) Cellular Immunology, Vol. 254: 85-90). However, treatment of autoimmune diseases supplementing with IFN-γ was ambivalent due to its broad biological effects causing unwanted activities. Further, it is clinically used to enhance immunity in patients with chronic granulomatous disease with good efficacy. Potential side effects include fever, hypotension, and flu-like symptoms (Holland S M, (2009) Clinic Rev Allerg Immunol, 38: 3-10). It is also thought to be beneficial as treatment for brain tumor immunotherapy (Hague A et al., (2007) Neurochem Res, 32: 2203-2209).

Interleukins are a group of multifunctional cytokines that are produced by a variety of lymphoid and non-lymphoid cells of the immune system to mediate communication between the immune cells and are particularly important to promote immune responses as inflammation and in the hematopoeisis. An example of a proinflammatory classified interleukin is IL-6. Its dysregulation can contribute to the induction and maintenance of several diseases such as rheumatoid arthritis and inflammatory bowel disease (Heinrich P C et al., (2003) Biochem. J., 1374: 1-20). IL-6 has also anti-inflammatory properties by for example inhibiting TNFs (Opal S M and DePalo V A, (2000) Chest Anti-inflammatory cytokines, 117: 932-4) reflecting the challenge of using a cytokine as therapy or as target for immunotherapy. In contrast, IL-10 is classified as an anti-inflammatory cytokine and is produced by monocytes, macrophages, mast cells, T and B lymphocytes, and dendritic cells. It is believed that it can suppress the production of pro-inflammatory cytokines and plays a central role in the regulation of immune responses. It also has broad implications in the development of certain inflammatory diseases, most noticeably allergy and asthma (Hawrylowicz C M and O'Garra A, (2005) Nat Rev Immunol, 202: 1459-63; Ogawa Y et al., (2008) Curr Mol Med, 8: 437-45). Numerous clinical studies have indicated that there is a general lack of sufficient levels of IL-10 in asthmatic patients which may contribute to a more intensive inflammation as shown by K. Tomita and colleagues who described that levels of IL-10 and IL-10 producing cells were significantly reduced in patients with severe persistent asthma when compared to mild asthma (Tomita K et al., (2002) Clin Immunol, 102: 258-66). It is also believed that corticosteroids, widely used anti-inflammatory compounds, exert their anti-inflammatory effects in part by enhancing IL-10 production (Richards D F et al., (2000) Eur J Immunol, 30: 2344-54). In corticosteroid resistant asthmatic patients, corticosteroids failed to induce IL-10 synthesis suggesting a strong link between induction of IL-10 synthesis and efficacy of corticosteroids (Hawrylowicz C M et al., (2002) J Allergy Clin Immunol, 109: 369-70). Experiments from D. Hesse and colleagues (Hesse D et al., (2010) Europ. J. Neurol., 15: 1-7) indicated that the expression of endogenous IFN-β induces the expression of IL-10 in MS and that the expression of IL-10 negatively correlates with the disease activity suggesting that IL-10 expression is associated with the dampening of the inflammatory response. Furthermore, in patients with evolved neutralizing antibodies (NAbs), IL-10 expression is reduced.

The use of cell surface antigens as therapeutic targets is another growing area of modulating the immune system.

Using antibody-related therapies can have several options such as binding to a specific target molecule on the cell surface to trigger cellular mechanisms such as apoptosis or activation pathways (immunotherapy), or simply binding to a target on the cell surface for delivery of an agent to the specific cell type, e.g. cytostatic agent (immuno-chemotherapy). Immunotherapy is used in the treatment or alleviation of many immunological diseases or conditions, such as cancer, inflammatory diseases such as asthma and allergy and also autoimmune disorders such as multiple sclerosis.

WO2010/053433 A1 describes the potential of specific oligonucleotides in up-regulating the expression of certain cell surface markers or cell surface antigens such as CD20, CD23, CD69 and CD80. The pre-incubation of PBMC isolated from CLL patients significantly increased the rate of apoptosis in human B-cells mediated by a monoclonal antibody directed against CD20 (rituximab).

WO2010/053430 A1 describes the capability of specific oligonucleotides to influence the properties and behaviour of polymorphonuclear cells, in particular the recruitment and/or migration of polymorphonuclear cells to a site of inflammation, and that they through this mechanism have utility in the prevention, treatment and/or alleviation of various diseases such as ischemia.

The challenges of immunotherapy and treatment with cytokines are the occurring side effects and the observed immunogenicity of these protein therapeutics even of fully human protein drugs (Vial T and Descotes J, (1994) Drug Saf, 10: 115-20; Scott D W and De Groot A S, (2010) ANN Rheum Dis, 69: 72-76). Especially, for the treatment within IFN-$\alpha$ it was suggested that the efficacy of the treatment has to be increased while the toxicity should be decreased (Sarasin-Filipowicz M, (2010) Swiss Med Wkly, 140: 3-11). The usage of endogenous induced IFN-$\alpha$ could be more effective and tolerable. P. Sfriso and colleagues could for example show that exposure to fungi is positive for the treatment of inflammatory bowel disease (Sfriso P et al., (2010) J Leuk Biol, 87: 385-95). Fungi are a natural source of foreign DNA and proteins, inducing endogenous cytokine production. Endogenous induction of cytokines could give beneficial effects without unwanted induced activities. Another aspect is that IFN-$\alpha$, for example, exists in numerous subforms, however through endogenously induced expression all subforms will be expressed in their natural way. It could be shown in corticosteroid-resistant asthma patients that IL-10 is up-regulated after IFN-$\alpha$ treatment and the authors suggest that the beneficial effects of IFN-$\alpha$ lies in the production of IL-10 (Simon H U et al., (2003) Allergy, 58: 1250-1255). IL-10 has less side effects than IFN-$\alpha$ and therefore could be a better treatment option. Chen and collegues described the opposite functions of IL-10 and IFN-$\gamma$ in a subform of CD4+ T-cells while they are working together in the disease management of chronic infections (Chen J and Liu X S, (2009) J Leuk Biol, 86: 1305-10). These examples demonstrate how different cytokines with different biological functions can act together to modulate the pathogenesis of a disease or to maintain the fine balance in an immune response. A more effective treatment option could be a combination of different cytokines or a way to induce different cytokines endogenously. There is clearly a need to provide methods and oligonucleotides that can induce the endogenous expression of specific cytokines.

DESCRIPTION OF THE INVENTION

Although synthesized oligonucleotides may interact with the cellular receptor (TLR9), the inventors have surprisingly identified that various synthetic oligonucleotides can induce different patterns of cytokine expression in human PBMCs wherein the functionality is dependent on the tertiary structure of the oligonucleotides and not on the primary structure or the content of any specific sequence feature as for example the dinucleotide CpG. Non-CpG oligonucleotides can induce cytokine expression and some CpG containing oligonucleotides cannot. The inventors have developed a method for identifying new oligonucleotides that can induce preferably specific cytokines, wherein said functionality is dependent on their tertiary structure. The oligonucleotides would be useful in treatment of diseases related to deficiencies or imbalance in these cytokines.

The present invention refers to methods of identifying oligonucleotides that adopts a certain tertiary structure, and thereby are able to modulate the immune system, irrespective of primary structure. The primary structure of the oligonucleotides identifiable by the methods of the invention may or may not fall into any of previously known ODN primary structure classes but as long as they have the desired tertiary structure described by the invention, they are unified by both the tertiary structure and their capability to modulate the immune system, such as inducing particular cytokines.

In the present invention, there is provided methods for identifying oligonucleotides capable of modulating the immune system in a mammalians comprising analyzing which tertiary structural type said oligonucleotide adopts, in phosphate-buffered saline solution. Typically, the method is capable of identifying oligonucleotides characterized in that they form at least 40% of telomeric G-quadruplex tetramer type of tertiary structure. This group of oligonucleotides are surprisingly active in stimulation of IFNs compared to similar oligonucleotides (in primary structure) that do not form a telomeric G-quadruplex tetramer type of tertiary structure. Such oligonucleotides with nearly identical primary structure surprisingly differ strongly in their capability of inducing IFNs production. Particularly the ODNs identifiable by the methods of the present invention form at least 40% of telomeric G-quadruplex tetramer type of tertiary structure, independently of their primary structure and these are able to induce specific cytokine profiles, in particular IFN-$\alpha$, IFN-$\beta$ and/or IFN-$\gamma$. Further, the method is capable of identifying oligonucleotides characterized in that they form at least 45% of non-G-quadruplex dimer type of tertiary structure. This group of oligonucleotides are surprisingly active in stimulation of cytokines IL-6 and/or IL10, compared to similar oligonucleotides (in primary structure) that do not form a non-G-quadruplex dimer type of tertiary structure. Such oligonucleotides with nearly identical primary structure surprisingly differ strongly in their capability of inducing IL-6 and/or IL10 production. Particularly the ODNs identifiable by the methods of the present invention form at least 45% of non-G-quadruplex dimer type of tertiary structure, independently of their primary structure and these are able to induce specific cytokine profiles, in particular IL-6 and/or IL-10.

The inventors have set out to develop a method for identification of novel oligonucleotides capable of endogenously modulating the immune system in a mammalian subject depending on the tertiary structure adopted in solution and, therefore useful in the treatment of inflammatory and autoimmune diseases. Other objects underlying the invention, as well as advantages associated with the invention, will become evident to the skilled person upon study of the description, examples and claims.

SHORT DESCRIPTION OF THE DRAWINGS

FIGS. 1A-1H depict the aligned CD spectra of reference oligonucleotides (refs #1-8) used in the calculation of the relative structural composition of the CD spectra of the oligonucleotides of the invention. The wavelength of the spectra is represented on the abscissa axis and corresponding molar ellipticity value is represented on the ordinate axis.

FIGS. 2A-2G depict the molar ellipticity of 3 oligonucleotides with major contribution telomeric G-quadruplex tetramer type of tertiary structure (IDX-9054, IDX-9059, IDX-9133), 3 oligonucleotides with less than 40% contribution of telomeric G-quadruplex tetramer type of tertiary structure (IDX-0445, IDX-0465, IDX-9134) and a negative control sample (IDX-9011). The experimental data overlaid on the calculated CD spectra input of standard components; CD spectra indicated as follows: sample—experimental measured spectra of oligonucleotide, #1—standard component 1 (SEQ ID NO 1); #2—standard component 2 (SEQ ID NO 2); #3—standard component 3 (SEQ ID NO 3); #4—standard component 4 (SEQ ID NO 4); #5—standard component 5 (SEQ ID NO 5); #6—standard component 6 (SEQ ID NO 6); #7—standard component 7 (SEQ ID NO 7); #8—standard component 8 (SEQ ID NO 8). The samples represent oligonucleotides with SEQ ID NO 7 (IDX-9011); SEQ ID NO 81 (IDX-9054); SEQ ID NO 91 (IDX-0445); SEQ ID NO 59 (IDX-0465); SEQ ID NO 83 (IDX-9059); SEQ ID NO 80 (IDX-9133); and SEQ ID NO 94 (IDX-9134). The wavelength of the spectra is represented on the abscissa axis and corresponding molar ellipticity value is represented on the ordinate axis.

FIG. 3A-3J depict the molar ellipticity of 8 oligonucleotides with major contribution of non-G-quadruplex dimer type of tertiary structure (IDX-0910, IDX-0912, IDX-9022, IDX-0475, IDX-0480, IDX-9071, IDX-0001, IDX-9024), one oligonucleotide with less than 45% contribution of non-G-quadruplex dimer type of tertiary structure (IDX-0465) and a negative control sample (IDX-9011). The experimental data overlaid on the calculated CD spectra input of standard components; CD indicated as follows: sample—experimental measured spectra of oligonucleotide, #1—standard component 1 (SEQ ID NO 1); #2—standard component 2 (SEQ ID NO 2); #3—standard component 3 (SEQ ID NO 3); #4—standard component 4 (SEQ ID NO 4); #5—standard component 5 (SEQ ID NO 5); #6—standard component 6 (SEQ ID NO 6); #7—standard component 7 (SEQ ID NO 7); #8—standard component 8 (SEQ ID NO 8). The samples represent oligonucleotides with SEQ ID NO 7 (IDX-9011); SEQ ID NO 56 (IDX-0910); SEQ ID NO 57 (IDX-0912); SEQ ID NO 44 (IDX-9022); SEQ ID NO 10 (IDX-0475); SEQ ID NO 11 (IDX-0480); SEQ ID NO 47 (IDX-9071); SEQ ID NO 48 (IDX-0001); SEQ ID NO 49 (IDX-9024) and SEQ ID NO 59 (IDX-0465). The wavelength of the spectra is on the abscissa axis and corresponding molar ellipticity value is on the ordinate axis.

FIG. 4A-4B represent an example of calculation of the relative composition of the CD spectra of IDX 9022 (SEQ ID NO 44) applying a fitting analysis using computer program for the mathematical decomposition of experimental data. FIG. 4A: Molar ellipticity of IDX 9022 (SEQ ID NO 44) overlaid on the aligned experimental measured CD spectra of the oligonucleotides used as standard components in the calculation of the relative structural composition of the CD spectra of the samples. FIG. 4B: Molar ellipticity of IDX 9022 (SEQ ID NO 44) overlaid on the aligned theoretically calculated fitting CD spectra of standard components and on the fitting curve of sum of the theoretically calculated CD spectra of standard components. Inserted table indicates calculated fitting CD spectra input (%) of standard components. CD spectra indicated as follows: sample—experimental measured spectra of IDX 9022 (SEQ ID NO 44) oligonucleotide, fit—fitting curve of sum of the calculated CD spectra input of standard components, #1—standard component 1 (SEQ ID NO 1); #2—standard component 2 (SEQ ID NO 2); #3—standard component 3 (SEQ ID NO 3); #4—standard component 4 (SEQ ID NO 4); #5—standard component 5 (SEQ ID NO 5); #6—standard component 6 (SEQ ID NO 6); #7—standard component 7 (SEQ ID NO 7); #8—standard component 8 (SEQ ID NO 8). The wavelength of the spectra is on the abscissa axis and corresponding molar ellipticity value is on the ordinate axis.

FIGS. 5A-5B represent an example of calculation of the relative composition of the CD spectra of IDX 9054 (SEQ ID NO 81) applying a fitting analysis using computer program for the mathematical decomposition of experimental data. FIG. 5A: Molar ellipticity of IDX 9054 (SEQ ID NO 81) overlaid on the aligned experimental measured CD spectra of the oligonucleotides used as standard components in the calculation of the relative structural composition of the CD spectra of the samples. FIG. 5B: Molar ellipticity of IDX 9054 (SEQ ID NO 81) overlaid on the aligned theoretically calculated fitting CD spectra of standard components and on the fitting curve of sum of the theoretically calculated CD spectra of standard components. Inserted table indicates calculated fitting CD spectra input (%) of standard components. The wavelength of the spectra is on the abscissa axis and corresponding molar ellipticity value is on the ordinate axis.

DETAILED DESCRIPTION OF THE INVENTION

Figure 1A:
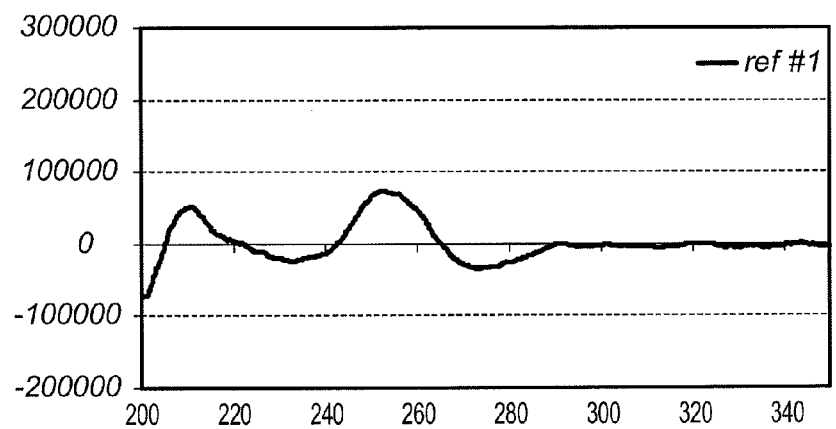

Before the invention is described in detail, it is to be understood that this invention is not limited to the particular compounds described or process steps of the methods described since compounds and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a sequence" includes more than one such sequence, and the like.

Further, the term "about" is used to indicate a deviation of +/−2 percent of the given value, preferably +/−5 percent and most preferably +/−10 percent of the numeric values, when applicable.

The phrase "capable of modulating the immune system" is used to describe a function, wherein a substance is capable to alter an immune response. Immunomodulation is an alteration, adjustment or regulation of the immune response. An immunomodulator is a substance that has an effect on the immune system in form of immunostimulation or immunosupression or both. The modulation of the immune system may represent an increase or a balancing of the levels of cytokines. This effect can be mediated by, but is not limited to, cytokines (lymphokines, chemokines, interleukins, interferons), cell surface markers, receptors, prostaglandins and hormones. These changes in the immune response can be for example measured through the release of cytokines, expression changes of cell surface markers or other physiological parameters as proliferation. The substance or immunomodulator is preferably an oligonucleotide.

The term "oligonucleotide" refers to a nucleic acid polymer, typically with from 8 to 120 bases, preferably of about 12 to about 30 nucleotides. Preferably, said oligonucleotide represents a DNA oligonucleotide, which should be interpreted as being equal to an oligodeoxyribonucleotide or an oligodeoxyribonucleic acid (ODN).

The phrase "tertiary structural type" refers to different spatial organizations that an oligonucleotide may adopt. In relation to the present invention, the following described types of tertiary structure are relevant: telomeric G-quadruplex tetramer type; fragile X G-quadruplex dimer type; telomeric G-quadruplex dimer type form 1; telomeric G-quadruplex dimer type form 2; non-G-quadruplex dimer type; G-quadruplex basket monomer type; random type and G-quadruplex chair monomer type. These structural types are further described and defined below.

The phrase "adopts, in phosphate-buffered saline solution" refers to that the tertiary structural type of the oligonucleotides of the invention adopts a particular tertiary structure type that is measureable in a phosphate-buffered saline solution. A phosphate-buffered saline solution refers here to a buffer solution system relevant or similar to physiological conditions such as a phosphate-buffered saline solution (PBS) comprising 10 mM phosphate buffer (pH 7.4) with 140 mM NaCl and 27 mM KCl. Other phosphate-buffered saline solutions or aqueous buffer solutions with similar physiological properties may also be used.

The experiments related to the present invention are typically carried out at room temperature. However, they can also be carried out at 37° C.

The testing of the capability for oligonucleotides of the invention to modulate the immune system in mammalian subjects, may be carried out as described below in Example 2.

The invention relates to the surprising concept that if a certain oligonucleotide forms a certain tertiary structure, at least to a certain percentage in a composition, it is capable of modulating the immune system, such as increasing levels of cytokines. Therefore, there is provided methods for identification of such oligonucleotides. In order to determine the tertiary structure, samples were prepared and analyzed by circular dichroism (CD) measurement. The results were compared to the results of CD measurements of a number of reference oligonucleotides that are capable of, and established to form particular tertiary structures. The sequences of these reference oligonucleotides are disclosed in Table 1.

TABLE 1

Tertiary structure references for CD spectra analysis.

| SEQ ID NO | Sequence 5'-3' | Structure type | Ref. number | IDX-No |
|---|---|---|---|---|
| 1 | TGGGGT | telomeric G-quadruplex tetramer | #1 | 0400 |
| 2 | GCGGTTTGCGG | fragile X G-quadruplex dimer | #2 | 0405 |
| 3 | GGGTTTTGGG | telomeric G-quadruplex dimer form 1 | #3 | 0415 |

TABLE 1-continued

Tertiary structure references for CD spectra analysis.

| SEQ ID NO | Sequence 5'-3' | Structure type | Ref. number | IDX-No |
|---|---|---|---|---|
| 4 | GGGGTTTTGGGG | telomeric G-quadruplex dimer form 2 | #4 | 0420 |
| 5 | GCATGCT | non-G-quadruplex dimer | #5 | 0430 |
| 6 | GGTTTTGGTTTTGGTTTTGG | G-quadruplex basket monomer | #6 | 0435 |
| 7 | T*C*A*CGACCGTCAAAC*T*C*C | random | #7 | 9011 |
| 8 | GGTTGGTGTGGTTGG | G-quadruplex chair monomer | #8 | 0410 |

* = phosphorothioate modification

The properties set out in Table 1, and adhered to throughout this specification, are to be understood as:

Telomeric G-Quadruplex Tetramer Type

Oligonucleotide TGGGGT is derived from the *O. nova* telomeric sequence. Previous work using both X-ray crystallographic (XRC) and nuclear magnetic resonance (NMR) has shown that it forms a tetrameric structure (see e.g. Phillips, K., et al. (1997) J. Mol. Biol., 273, 171-182; Aboul-ela, F. et al. (1994) J. Mol. Biol., 243, 458-471; Aboul-ela, F. et al. (1992) Nature, 360, 280-282). Thus, the oligonucleotide TGGGGT (SEQ ID NO 1—reference #1) serves as reference oligonucleotide for a telomeric G-quadruplex tetramer type and its CD spectrum is depicted in FIG. 1A.

Fragile X G-Quadruplex Dimer Type

Figure 1B:
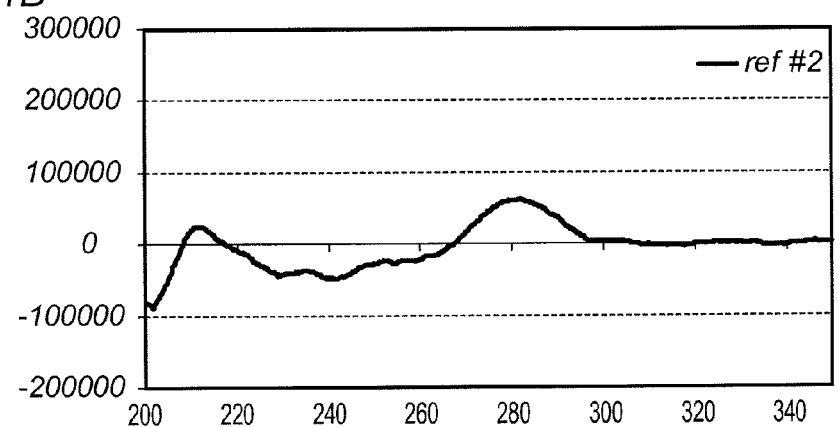

Oligonucleotide GCGGTTTGCGG represents the fragile X gene repeat sequence and has been shown to form a specific dimeric structure (see Kettani, A. et al. (1995) J. Mol. Biol., 254, 638-65). Thus, the oligonucleotide GCGGTTTGCGG (SEQ ID NO 2—reference #2) serves as reference oligonucleotide for a Fragile X G-quadruplex dimer type and its CD spectrum is depicted in FIG. 1B.

Telomeric G-Quadruplex Dimer Type Form 1

Figure 1C:
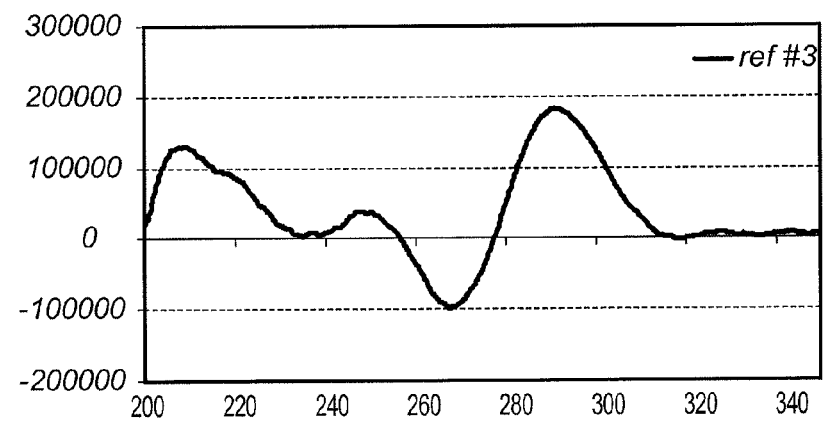

Oligonucleotide GGGTTTTGGG is derived from the *O. nova* telomeric sequence. NMR studies showed that it forms a specific dimeric G-quadruplex structure (see e.g. Scaria, P. V. et al. (1992) Proc. Natl. Acad. Sci. USA, 89, 10336-10340; Keniry, M. A. et al. (1995) Eur. J. Biochem., 233, 631-643; Hud, N. V. et al. (1996) Biochemistry, 35, 15383-15390). Thus, the oligonucleotide GGGTTTTGGG (SEQ ID NO 3—reference #3) serves as reference oligonucleotide for a telomeric G-quadruplex dimer type form 1 and its CD spectrum is depicted in FIG. 1C.

Telomeric G-Quadruplex Dimer Type Form 2

Figure 1D:
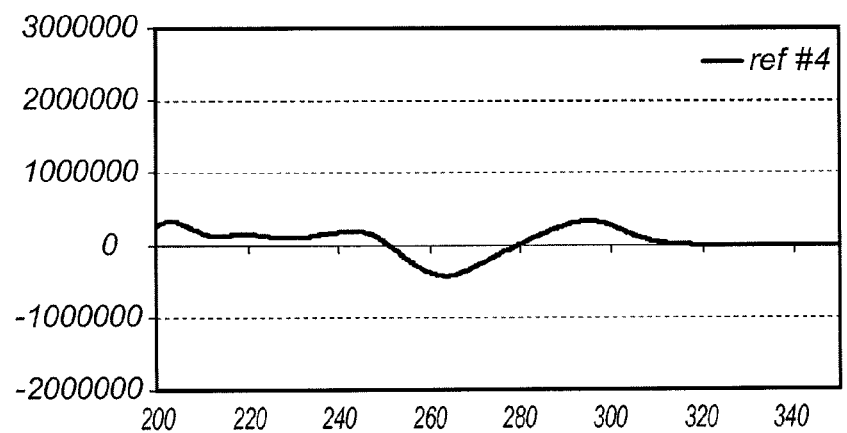

Oligonucleotide GGGGTTTTGGGG is derived from the *O. nova* telomeric sequence. Both XRC and NMR studies showed that it forms a specific G-dimeric non-GC structure (see e.g. Schultze, P. et al. (1999) Nucleic Acids Res., 27, 3018-3028; Kang, C. et al. (1992) Nature, 356, 126-131; Smith, F. W. and Feigon, J. (1993) Biochemistry, 32, 8682-8692; Haider, S. et al. (2002) Mol. Biol., 320, 189-200). Thus, the oligonucleotide GGGGTTTTGGGG (SEQ ID NO 4—reference #4) serves as reference oligonucleotide for a telomeric G-quadruplex dimer type form 2 and its CD spectrum is depicted in FIG. 1D.

Non-G-Quadruplex Dimer Type

Figure 1E:
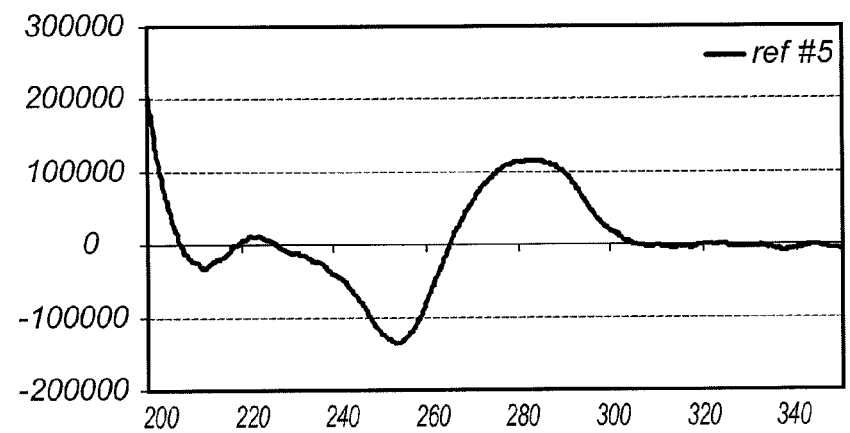

Oligonucleotide GCATGCT forms a specific quadruplex dimeric structure that does not involve G-quadruplex formation (see Leonard, G. A. et al. (1995) Structure, 3, 335-340). Thus, the oligonucleotide GCATGCT (SEQ ID NO 5—reference #5) serves as reference oligonucleotide for a non-G-quadruplex dimer type and its CD spectrum is depicted in FIG. 1E.

G-Quadruplex Basket Monomer Type

Figure 1F:
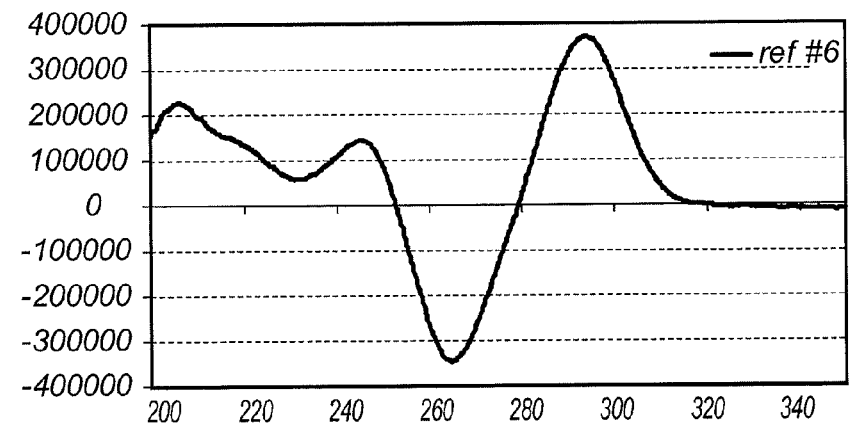

Oligonucleotide GGTTTTGGTTTTGGTTTTGG forms a specific monomeric G-quadruplex structure that was shown using NMR analysis (see Marathias, V. M. and Bolton, P. H. (1999) Biochemistry, 38, 4355-4364). Thus, the oligonucleotide GGTTTTGGTTTTGGTTTTGG (SEQ ID NO 6—reference #6) serves as reference oligonucleotide for a G-quadruplex basket monomer type and its CD spectrum is depicted in FIG. 1F.

Random Type

Figure 1G:
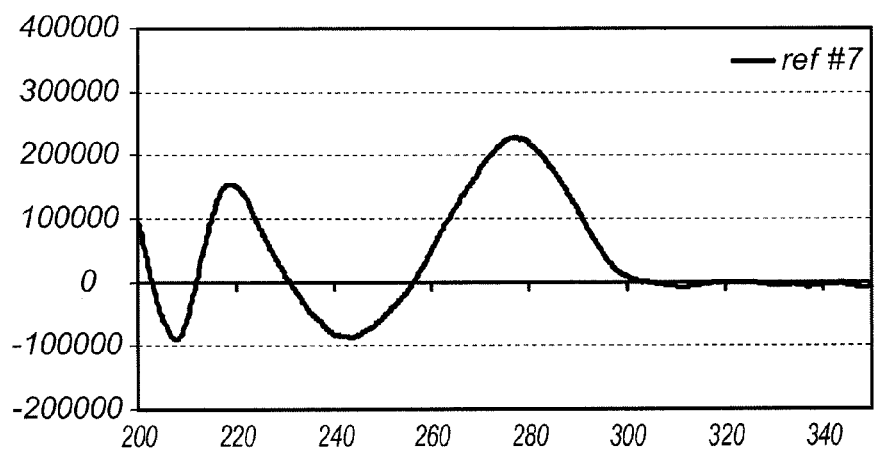

Oligonucleotide T*C*A*CGACCGTCAAAC*T*C*C designed by the inventors and is characterised by CD spectroscopy. It shows CD spectra characteristic for DNA that has random coil structure but doesn't form any particular specific tertiary structure. The oligonucleotide T*C*A*CGACCGTCAAAC*T*C*C (SEQ ID NO 7—reference #7) thus serves as reference oligonucleotide for a random type and its CD spectrum is depicted in FIG. 1G.

G-Quadruplex Chair Monomer Type

Figure 1H:
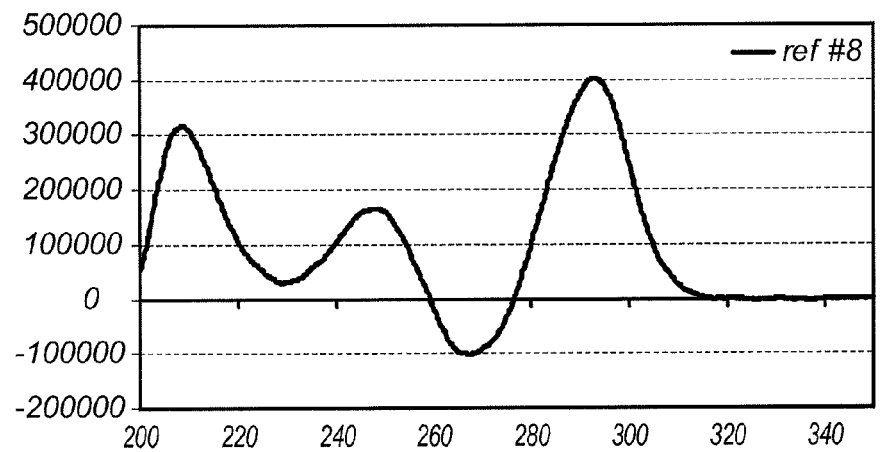
Figure 2A:
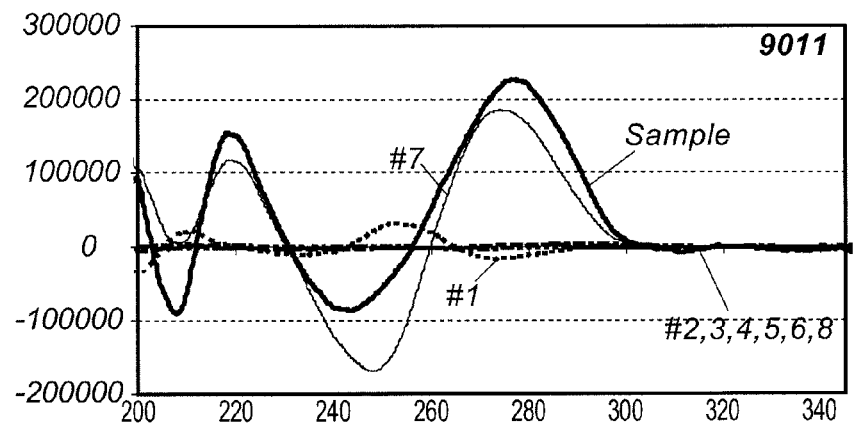
Figure 2B:
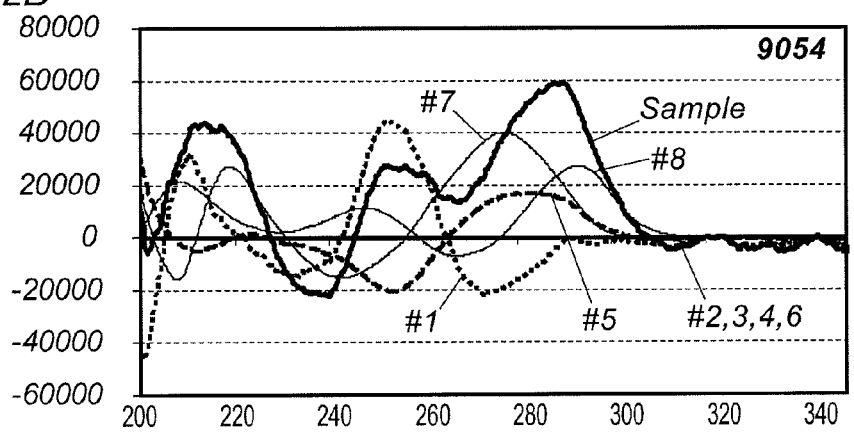
Figure 2C:
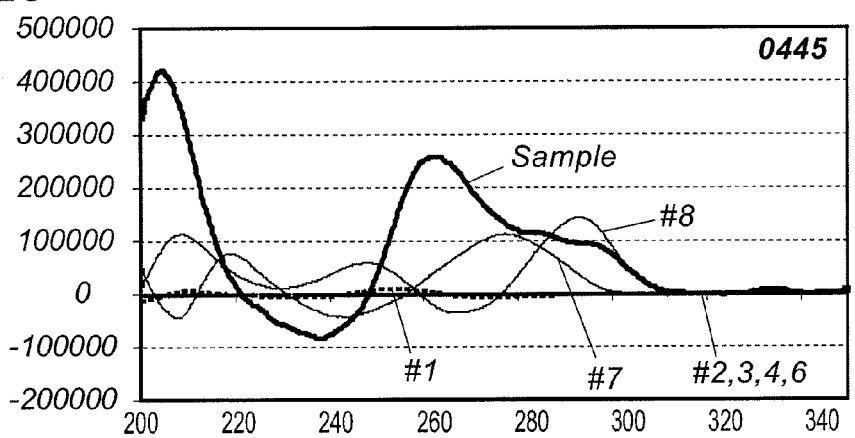
Figure 2D:
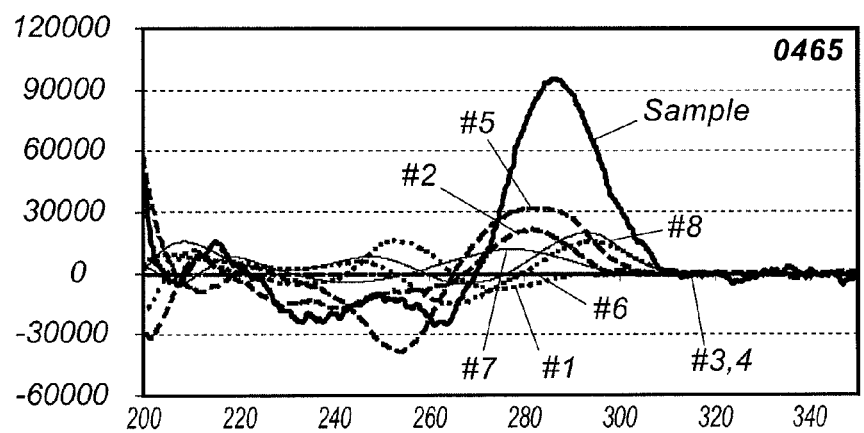
Figure 2E:
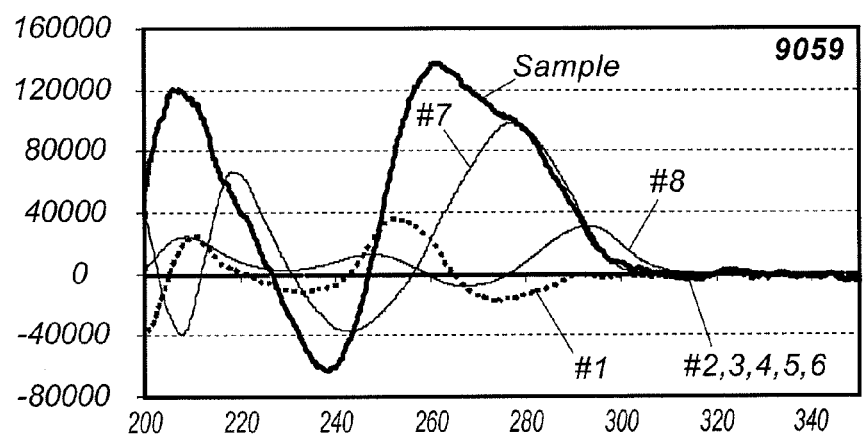
Figure 2F:
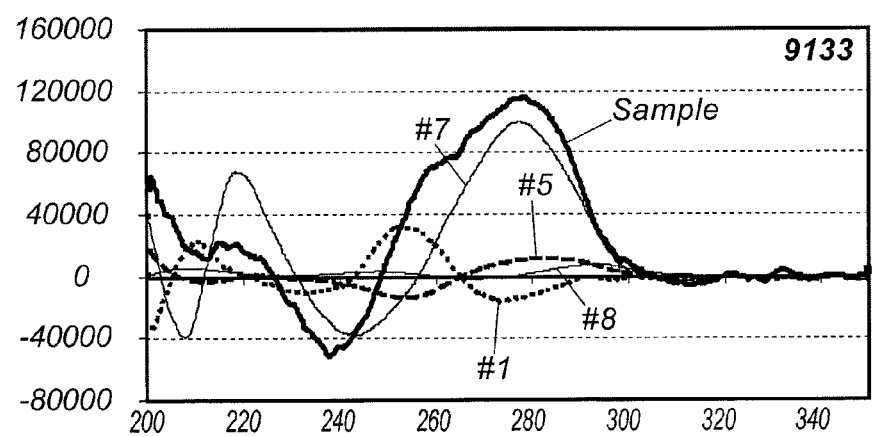
Figure 2G:
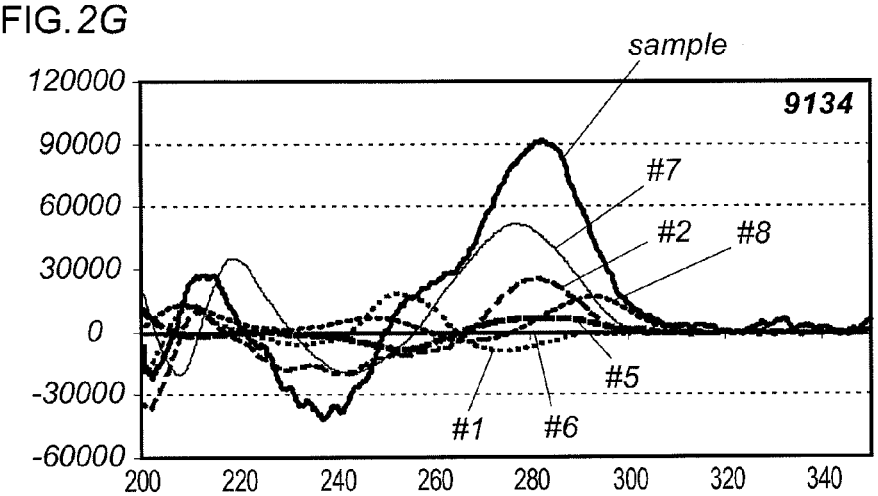
Figure 3A:
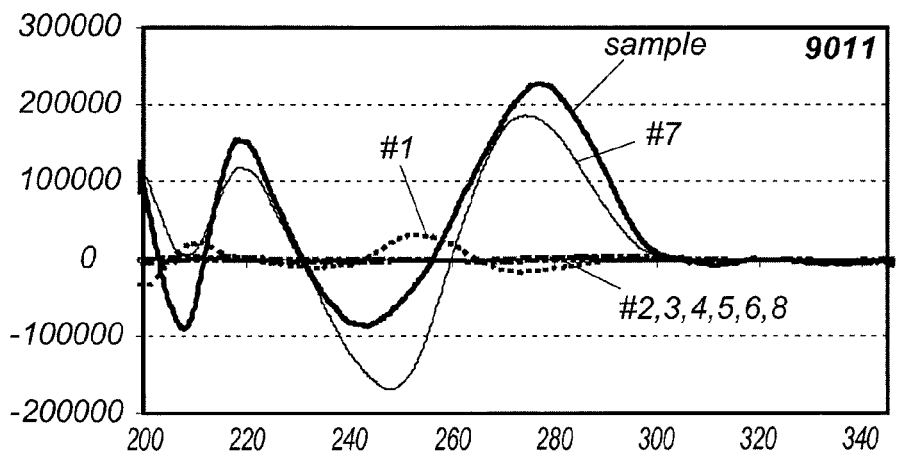
Figure 3B:
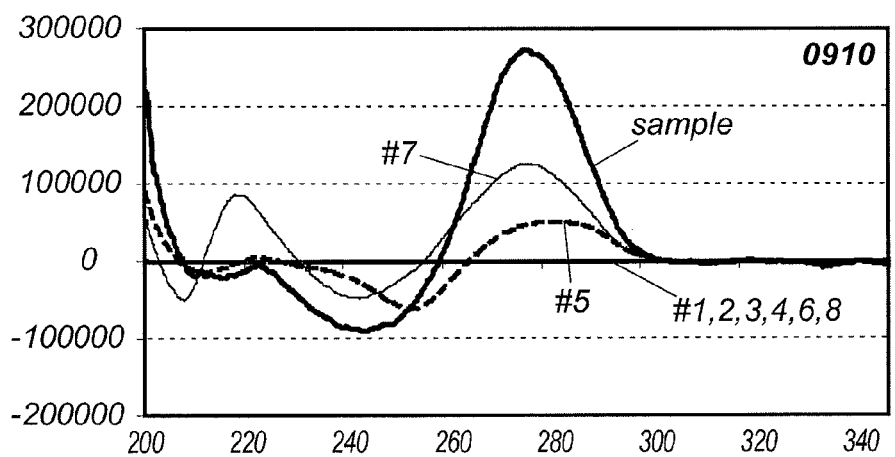
Figure 3C:
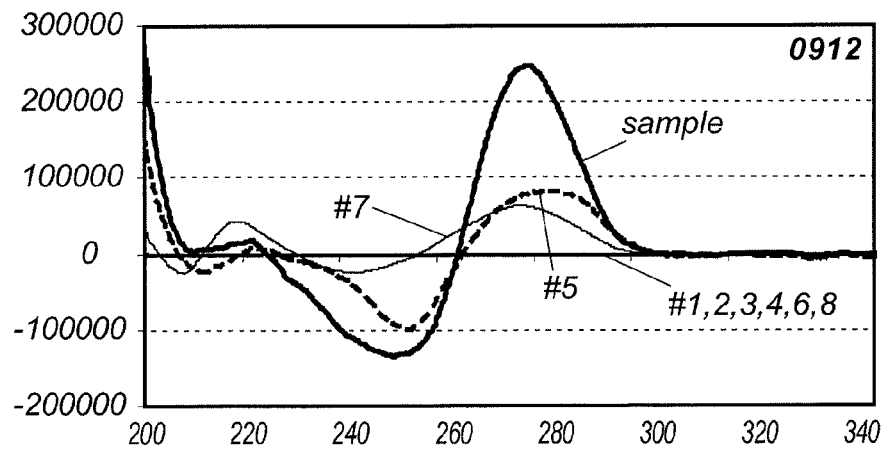
Figure 3D:
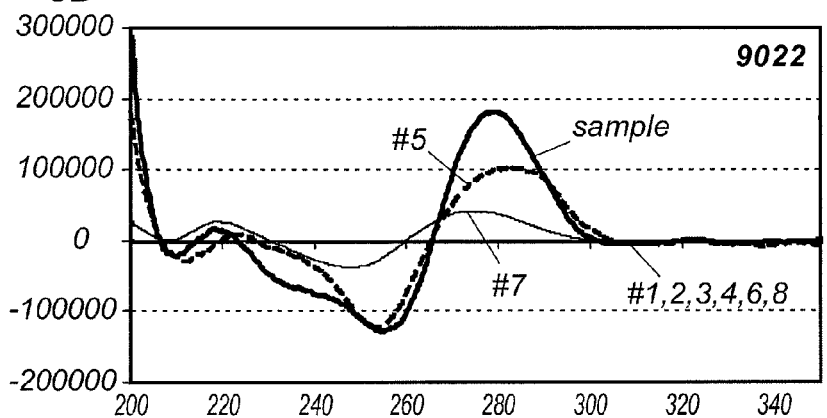
Figure 3E:
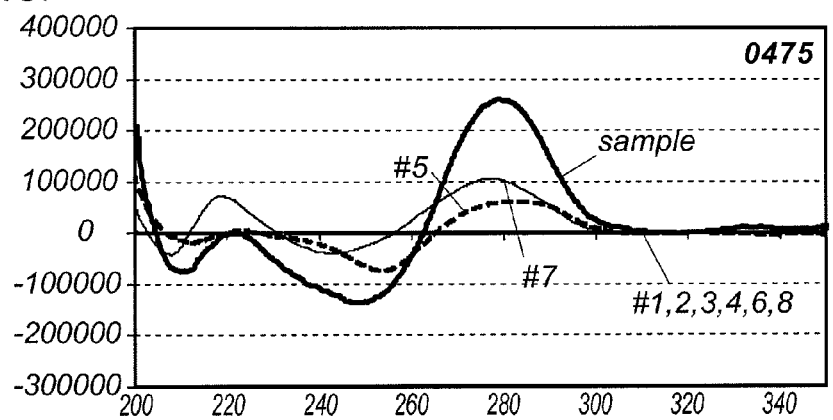
Figure 3F:
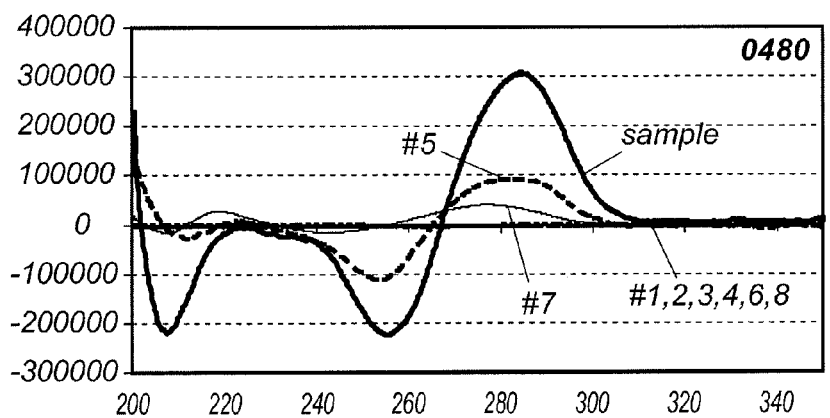
Figure 3G:
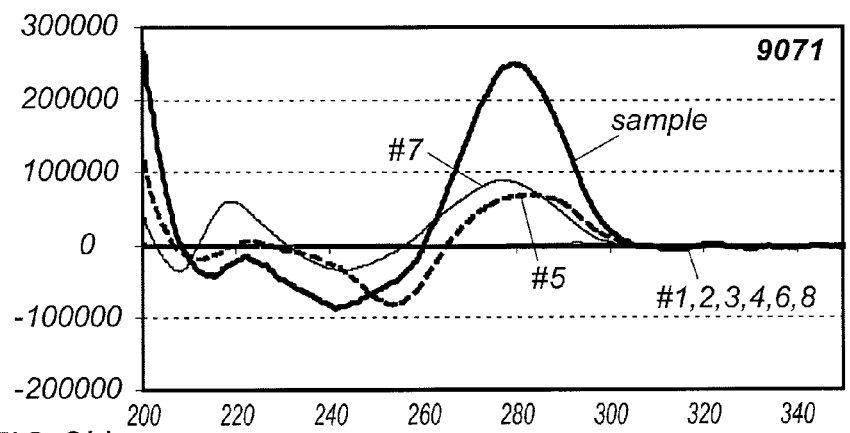
Figure 3H:
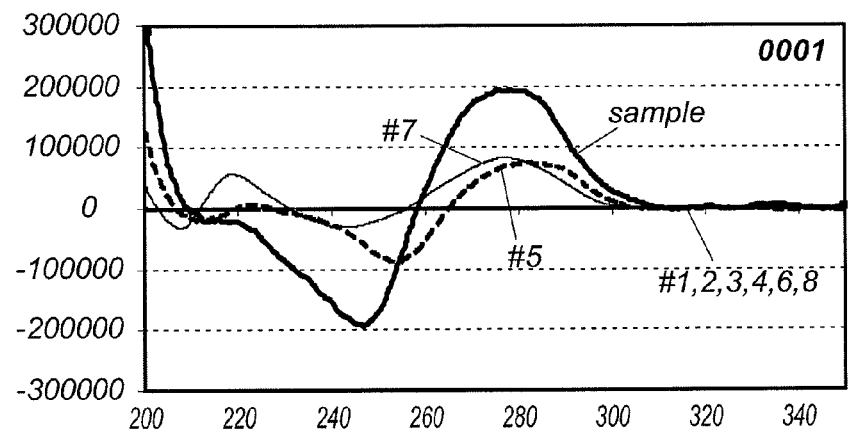
Figure 3I:
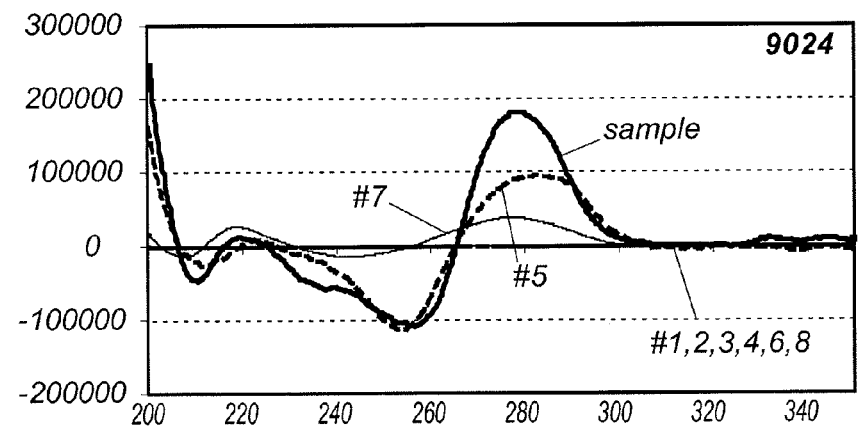
Figure 3J:
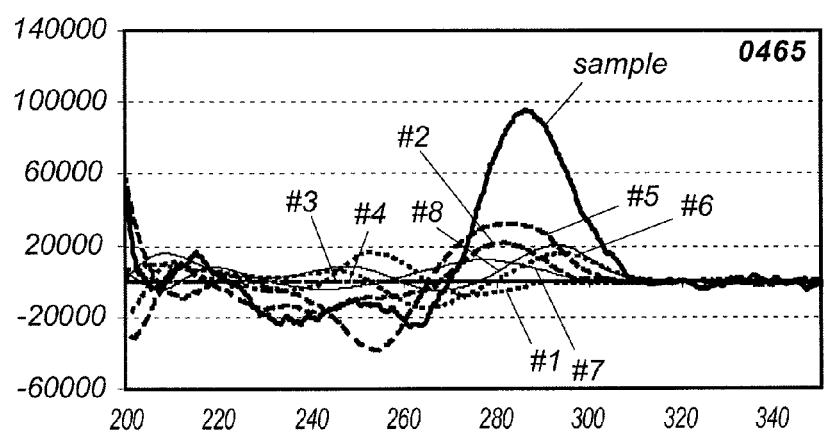

Oligonucleotide GGTTGGTGTGGTTGG is known as the thrombin-binding aptamer. It was created by an in vitro selection approach. It forms a monomeric G-quadruplex structure that was shown by both NMR and crystal structures (see Padmanabhan, K. and Tulinsky, A. (1996) Acta Crystallogr. D, 52, 272-282; Kelly, J. A. et al. (1996) J. Mol. Biol., 256, 417-422; Macaya, R. F. et al. (1993) Proc. Natl. Acad. Sci. USA, 90, 3745-3749; Padmanabhan, K. et al. (1993) J. Biol. Chem., 268, 17651-17654). The oligonucleotide GGTTGGTGTGGTTGG (SEQ ID NO 8—reference #8) thus serves as reference oligonucleotide for a G-quadruplex chair monomer type and its CD spectrum is depicted in FIG. 1H.

In a first aspect of the invention, there is provided a method for identifying an oligonucleotide capable of modulating the immune system in a mammalian subject comprising analyzing which tertiary structural type said oligonucleotide adopts, in phosphate-buffered saline solution. In said method, said capability of modulating the immune system can be analyzed by testing whether said oligonucleotide modulates the immune system in a mammalian subject. Said testing may be carried out in vitro.

In one embodiment of this aspect, there is provided a method for identifying an oligonucleotide capable of modulating the immune system in a mammalian subject comprising analyzing which tertiary structural type said oligonucleotide adopts, in phosphate-buffered saline solution, wherein said modulation of the immune system represents an increase of levels of cytokines, such as interferon-α, interferon-β, interferon-γ, IL-6 and/or IL-10. The modulation of the immune system may represent an increase or balancing the levels of cytokines. Preferably, said modulation of the immune system represents an increase of the levels of cytokines.

In another embodiment of this aspect, said oligonucleotide adopts, in phosphate-buffered saline solution, a tertiary structure of at least 45% of non-G-quadruplex dimer type. Preferably, said oligonucleotide adopts, in phosphate-buffered saline solution, at least 55%, more preferably 80%, even more preferably 90% of non-G-quadruplex dimer type. Said oligonucleotide are capable of modulation of the immune system by increasing levels of cytokines, in particular IL-6 and/or IL-10.

In another embodiment of this aspect, there is provided a method, wherein the amount of tertiary structural non-G-quadruplex dimer type is estimated by quantifying against the tertiary structural type of a reference oligonucleotide that adopts, in phosphate-buffered saline solution, non-G-quadruplex dimer type. Said reference oligonucleotide may represent an oligonucleotide of SEQ ID NO 5. The quantifying estimate is carried out such that the amount of structural non-G-quadruplex dimer type of the reference oligonucleotide is set at 100 percent.

In another embodiment of this aspect, there is provided an oligonucleotide, identifiable by the methods of said methods. Said oligonucleotide, preferably has at least one nucleotide that has a phosphate backbone modification. Said phosphate backbone modification preferably is a phosphorothioate or phosphorodithioate modification. Said oligonucleotide typically comprises of about 8 to about 120 nucleotides, preferably of about 12 to about 30 nucleotides.

In another embodiment of this aspect, said oligonucleotide adopts, in phosphate-buffered saline solution, a tertiary structure of at least 40% of telomeric G-quadruplex tetramer type. Preferably, said oligonucleotide adopts, in phosphate-buffered saline solution, at least 60%, preferably 80%, more preferably 90% of telomeric G-quadruplex tetramer type. Said oligonucleotide is capable of modulation of the immune system by increasing levels of cytokines, in particular interferons, such as interferon-α, interferon-β and/or interferon-γ. The modulation of the immune system may represent an increase or balancing the levels of said cytokines. Preferably, said modulation of the immune system represents an increase of the levels of said cytokines. The amount of tertiary structural telomeric G-quadruplex tetramer type is estimated by quantifying against the tertiary structural type of a reference oligonucleotide that adopts, in phosphate-buffered saline solution, a telomeric G-quadruplex tetramer type. Said reference oligonucleotide may represent an oligonucleotide of SEQ ID NO 1. The quantifying estimate is carried out such that the amount of structural telomeric G-quadruplex tetramer type of the reference oligonucleotide is set at 100 percent.

In another embodiment of this aspect, there is provided an oligonucleotide, identifiable by the methods of the invention. Said oligonucleotide, preferably has at least one nucleotide that has a phosphate backbone modification. Said phosphate backbone modification preferably is a phosphorothioate or phosphorodithioate modification. Said oligonucleotide typically comprises of about 8 to about 120 nucleotides, preferably of about 12 to about 30 nucleotides.

In another aspect of the invention, there is provided a method for identifying an oligonucleotide capable of modulating the immune system in a mammalian subject comprising analyzing which tertiary structural type said oligonucleotide adopts, in phosphate-buffered saline solution, wherein said modulation of the immune system represents an increase or decrease of levels of cell surface markers.

In another aspect of the invention, there is provided a method for identifying an oligonucleotide capable of modulating the immune system in a mammalian subject comprising analyzing which tertiary structural type said oligonucleotide adopts, in phosphate-buffered saline solution wherein said modulation of the immune system represents a change in the properties or behaviour of polymorphonuclear cells.

In another aspect of the invention, there is provided an oligonucleotide selected from the group consisting of SEQ ID NOs 60, 62, 67, 68, 70, 72, 74-77 and 79-80.

In another aspect of the invention, there is provided an oligonucleotide selected from the group consisting of SEQ ID NOs 76, 77 and 80.

In one embodiment of this aspect, there is provided said oligonucleotide for use in therapy.

In another embodiment of this aspect, there is provided said oligonucleotide for use in treating a disease where increasing or balancing the levels of cytokines are beneficial for said treatment.

In another embodiment of this aspect, there is provided said oligonucleotide for use in treating a disease where increasing the levels of cytokines are beneficial for said treatment.

In another aspect of the invention, there is provided an oligonucleotide selected from the group consisting of SEQ ID NOs 13-17, 19-22, 24-30, and 33-35.

In another aspect of the invention, there is provided an oligonucleotide selected from the group consisting of SEQ ID NOs 16, 28 and 33.

In one embodiment of this aspect, there is provided said oligonucleotide for use in therapy.

In another embodiment of this aspect, there is provided said oligonucleotide for use in treating a disease where increasing or balancing the levels of cytokines are beneficial for said treatment.

In another embodiment of this aspect, there is provided said oligonucleotide for use in treating a disease where increasing the levels of cytokines are beneficial for said treatment.

The methods of the invention have been tested and a number of novel oligonucleotides have been shown to being capable of modulating the immune system. The invention, therefore, makes available specific novel oligonucleotides. In one aspect of the invention there is provided oligonucleotides with sequences according to any one of sequences in Table 2.

In another aspect of the invention there is provided isolated oligonucleotides with sequences according to any one of SEQ ID NOs 13-17, 19-22, 24-30 and 33-35. These oligonucleotides have been identified to adopt, in phosphate-buffered saline solution, a tertiary structure composed of at least 45% of non-G-quadruplex dimer type. Further, these oligonucleotides have also been shown to be or of being capable of increasing levels of cytokines, such as IL-6 and/or IL-10. These particular oligonucleotides are presented in Table 2, which correlates the SEQ ID NOs with the nucleotide sequences and corresponding internal reference codes ("IDX-No").

TABLE 2

Active oligonucleotides with at least 45% of non-G-quadruplex dimer type.

| SEQ ID NO | Sequence 5'-3' | IDX-No |
|---|---|---|
| 9 | TCGTCGTTCTGCCATCGTCGTT | 0470 |
| 10 | T*T*G*TTGTTCTGCCATCGTC*G*T*T | 0475 |
| 11 | T*G*C*TGCTTCTGCCATGCTG*C*T*T | 0480 |
| 13 | T*C*G*TTCGTCTTGTTCGTTTGTTCG*T*G*G | 9013 |
| 14 | T*C*G*TTCGTCTTTTCGTTTTCGTCGG*C*G*C | 9014 |

TABLE 2-continued

Active oligonucleotides with at least 45% of non-G-quadruplex dimer type.

| SEQ ID NO | Sequence 5'-3' | IDX-No |
|---|---|---|
| 15 | T*C*C*GCGTTCGTTGTTCGTCG*C*G*G | 9017 |
| 16 | C*G*G*CGCGCCGTTCGTCGA*T*G*G | 9028 |
| 17 | C*G*G*CGCCGTTCGTCGA*T*G*G | 9029 |
| 18 | T*C*G*TCTGCTTGTTCGTCTTGTTC*G*T*C | 9069 |
| 19 | T*C*G*TTCGTCTGCTTGTTCGTCTTGTTC*G*T*C | 9070 |
| 20 | T*C*G*TTCGTCTTGTTCGTCGTC*T*G*C | 9072 |
| 21 | T*C*G*TTCGTCTTGTTCGTC*T*G*C | 9073 |
| 22 | T*T*T*TCGTCTGCTTTCGTTTCG*T*T*T | 9091 |
| 23 | T*G*C*C*A*T*T*C*G*T*C*G*T*T*C*T*C*G*T*C*G*T*T | 9100 |
| 24 | T*C*G*TCGTTCTGCCATCGT*C*G*T | 9138 |
| 25 | T*C*G*TCGTTCTCGTC*G*T*T | 9139 |
| 26 | T*C*G*TTCTGCTGAT*C*G*T | 9140 |
| 27 | T*C*G*TCGTTCTGTCGTC*G*T*T | 9141 |
| 28 | T*C*G*TCGTTCGTCGTC*G*T*T | 9142 |
| 29 | T*C*G*TCGTTGCTCGTC*G*T*T | 9143 |
| 30 | T*C*G*TCGTTCTCGT*C*G*T | 9144 |
| 33 | T*C*G*TCGTTCGTCGTTCGT*C*G*T | 9147 |
| 34 | T*T*C*TCGTTCTGCCATCGT*G*A*T | 9148 |
| 35 | T*C*G*TTCCGCCGAT*C*G*T | 9149 |
| 44 | T*C*G*TCGTTCTGCCATCGTC*G*T*T | 9022 |
| 45 | T*C*G*TTCGTCTTGTTCGTCTTGTTC*G*T*C | 9012 |
| 47 | T*C*G*TTCGTCTGCTTGTTC*G*T*C | 9071 |
| 48 | T*C*C*GCGTTCGGCCTCCTGGCG*C*G*G | 0001 |
| 49 | T*G*C*CATTCGTCGTTCTCGTC*G*T*T | 9024 |
| 50 | T*C*G*TCGTTCGGCCGATCG*T*C*C | 9038 |
| 51 | T*C*G*TTCGTCTTTCGTC*T*G*C | 9074 |
| 53 | T*T*T*CGTCTGCTTTCGTTTCG*T*T*T | 9092 |
| 54 | T*C*G*TCTGCTTTCGTC*T*G*C | 9095 |
| 56 | T*C*G*T*C*G*T*T*T*T*G*T*C*G*T*T*T*T*G*T*C*G*T*T | 0910 |
| 57 | T*C*G*TCGTTTTGTCGTTTTGTC*G*T*T | 0912 |

* = phosphorothioate modification

A number of oligonucleotides that do not modulate the immune system, in particular, they do not increase levels of cytokines in the presented assays are set out in Table 3. The tertiary structural types of these oligonucleotides were identified and it was shown that they had a different tertiary structural composition than the active oligonucleotides set out in Table 2. For these reasons, the oligonucleotides in Table 3 are designated as oligonucleotides with less than 45% non-G-quadruplex dimer type contribution.

TABLE 3

Oligonucleotides with less than 45% non-G-quadruplex dimer type contribution.

| SEQ ID NO | Sequence 5'-3' | IDX-No |
|---|---|---|
| 7 | T*C*A*CGACCGTCAAAC*T*C*C | 9011 |
| 59 | G*G*G*GTGCTCTGC*G*G*G | 0465 |
| 31 | A*A*C*GACGATGGCAGAACGA*C*G*A | 9153 |
| 32 | A*A*G*CAGCATGGCAGAAGCA*G*C*A | 9146 |
| 43 | G*C*C*TACTAAGTAATGACTGTC*A*T*G | 0495 |

* = phosphorothioate modification

In another aspect of the invention there is provided isolated oligonucleotides with sequences according to any one of sequences in Table 4, particularly isolated oligonucleotides with sequences according to any one SEQ ID NOs 60, 62, 67, 68, 70, 72, 74-77 and 79-80. These oligonucleotides have been identified to adopt, in phosphate-buffered saline solution, a tertiary structure composed of at least 40% telomeric G-quadruplex tetramer type. Further, these oligonucleotides have also been shown to being capable of increasing levels of interferons, such as interferon-α, interferon-β and/or interferon-γ. These particular oligonucleotides are presented in Table 4, which correlates the SEQ ID NOs with the nucleotide sequences and corresponding internal reference codes ("IDX-No").

TABLE 4

Active oligonucleotides with at least 40% of telomeric G-quadruplex tetramer type.

| SEQ ID NO | Sequence 5'-3' | IDX-No |
|---|---|---|
| 60 | T*C*T*GTCGTGTCCTTCTTT*G*G*C | 9008 |
| 62 | T*C*G*TCGTCTGAAGCCGC*G*G*C | 9019 |
| 67 | T*T*C*GTCGATGGCCG*G*C*C | 9027 |
| 68 | G*G*G*GTCGTCTGCTATCGATG*G*G*G | 9039 |
| 70 | G*G*T*CGTCTGCGACGATCGTCG*G*G*G | 9041 |
| 72 | G*G*G*GTCGTCTGCT*G*G*G | 9047 |
| 74 | G*G*G*GTCGTCTGCTC*G*G*G | 9049 |
| 75 | G*G*G*GTCGTCTGCCA*G*G*G | 9050 |
| 76 | G*A*T*CGTCCGGGTCCCGG*G*G*G | 9055 |
| 77 | G*A*T*CGTCCGCGG*G*G*G | 9057 |
| 78 | T*C*G*T*C*T*G*C*C*A*T*G*G*C*G*G*C*C*G*C*C | 9067 |
| 79 | T*C*G*TCTGCCATGGCGCGC*C*G*G | 9068 |
| 80 | G*A*T*CGTCCG*T*G*T | 9133 |
| 81 | G*G*G*GTCGTCTGC*G*G*G | 9054 |
| 82 | GGGGTCGTCTGCGGG | 0440 |

TABLE 4-continued

Active oligonucleotides with at least 40% of telomeric G-quadruplex tetramer type.

| SEQ ID NO | Sequence 5'-3' | IDX-No |
|---|---|---|
| 83 | G*A*T*CGTCCG*G*G*G | 9059 |
| 84 | G*G*G*GTCGCAGCT*G*G*G | 9004 |
| 85 | T*C*G*TCCATGGTCAGGGTCCCGG*G*G*G | 9005 |
| 89 | G*G*G*TCGTCTG*C*G*G | 9053 |
| 90 | G*A*T*CGTCCGTCGG*G*G*G | 9058 |

* = phosphorothioate modification

A number of oligonucleotides that do not modulate the immune system, in particular, they do not increase levels of interferons in the presented assays, are set out in Table 5. The tertiary structural types of these oligonucleotides were identified and it was shown that they had a different tertiary structural composition than the active oligonucleotides set out in Table 4. For these reasons, the oligonucleotides in Table 5 are designated as oligonucleotides with less than 40% contribution of telomeric G-quadruplex tetramer type.

TABLE 5

Oligonucleotides with less than 40% contribution of telomeric G-quadruplex tetramer type.

| SEQ ID NO | Sequence 5'-3' | IDX-No |
|---|---|---|
| 91 | G*G*G*G*T*C*G*T*C*T*G*C*G*G*G | 0445 |
| 31 | A*A*C*GACGATGGCAGAACGA*C*G*A | 9153 |
| 32 | A*A*G*CAGCATGGCAGAAGCA*G*C*A | 9146 |
| 59 | G*G*G*GTGCTCTGC*G*G*G | 0465 |
| 94 | G*A*T*GCTCTG*G*G*G | 9134 |
| 7 | T*C*A*CGACCGTCAAAC*T*C*C | 9011 |
| 43 | G*C*C*TACTAAGTAATGACTGTC*A*T*G | 0495 |

* = phosphorothioate modification

In another aspect of the invention there is provided an isolated oligonucleotide which adopts, in phosphate-buffered saline solution, a tertiary structure composed of at least 45% of non-G-quadruplex dimer type, said oligonucleotide being capable of balancing or increasing levels of cytokines in a mammalian subject upon administration to said subject. Preferably, said non-G-quadruplex dimer type is present in at least 55%, more preferably 80%, even more preferably 90% as non-G-quadruplex dimer type. Preferably, said oligonucleotide is capable of increasing levels of cytokines in a mammalian subject.

In one embodiment of this aspect, said oligonucleotide comprises at least one nucleotide that has a phosphate backbone modification. Preferably, said phosphate backbone modification is a phosphorothioate or phosphorodithioate modification.

In another embodiment of this aspect, said oligonucleotide comprises of about 8 to about 120 nucleotides, preferably of about 12 to about 30 nucleotides.

In another embodiment of this aspect, said cytokine represents IL-6 and/or IL-10.

In another embodiment of this aspect, said oligonucleotide is selected from the group consisting of SEQ ID NOs 13-17, 19-22, 24-30 and 33-35.

In another embodiment of this aspect, said oligonucleotide is selected from the group consisting of SEQ ID NOs 13-17 and 19-22.

In another embodiment of this aspect, said oligonucleotide is selected from the group consisting of SEQ ID NOs 16, 28 and 33.

In another embodiment of this aspect, there is provided said oligonucleotide for use in therapy.

In another embodiment of this aspect, there is provided said oligonucleotide for use in treating a disease where balancing or increasing the levels of cytokines are beneficial for said treatment.

In another embodiment of this aspect, there is provided said oligonucleotide for use in treating a disease where increasing the levels of cytokines are beneficial for said treatment.

In another embodiment of this aspect, there is provided said oligonucleotide for use in the treatment of diseases selected from inflammatory and/or autoimmune diseases.

In another embodiment of this aspect, there is provided said oligonucleotide for use in the treatment of diseases selected from inflammatory bowel disease, meningitis, allergy, atopic eczema, asthma and COPD.

In another embodiment of this aspect, there is provided use of said oligonucleotide, in the preparation of a medicament useful in the treatment where increasing or balancing the levels of cytokines are beneficial for said treatment.

In another embodiment of this aspect, there is provided use of said oligonucleotide, in the preparation of a medicament useful in the treatment of inflammatory and/or autoimmune diseases.

In another embodiment of this aspect, there is provided use of said oligonucleotide, in the preparation of a medicament useful in the treatment of a disease selected from inflammatory bowel disease, meningitis, allergy, atopic eczema, asthma and COPD.

In another embodiment of this aspect, there is provided use of said oligonucleotide, which use further comprises one or more additional agents effective in treating inflammatory and/or autoimmune diseases.

In another embodiment of this aspect, there is provided a method of treating a disease wherein increasing or balancing the levels of cytokines are beneficial for said treatment, comprising administering to a subject in need thereof, of said oligonucleotide.

In another embodiment of this aspect, there is provided a method of treating a disease wherein increasing the levels of cytokines are beneficial for said treatment, comprising administering to a subject in need thereof, of said oligonucleotide.

In another embodiment of this aspect, there is provided a method of treating inflammatory and/or autoimmune diseases, comprising administering to a subject in need thereof, of said oligonucleotide.

In another embodiment of this aspect, there is provided a method of treating a disease selected from inflammatory bowel disease, meningitis, allergy, atopic eczema, asthma and COPD, comprising administering to a subject in need thereof, of said oligonucleotide.

In another embodiment of this aspect, there is provided a method of treating said disease or diseases, which further comprises one or more additional agents effective in treating inflammatory and/or autoimmune diseases.

The term allergy in the present invention describes an inappropriate and excessive immunological reaction triggered by an allergen. Examples of allergens include, but are not limited to, pollen, animal dander, dust mites, food, insect stings, microorganisms, chemicals and medications.

In yet a further aspect of the invention there is provided an isolated oligonucleotide which adopts, in phosphate-buffered saline solution, a tertiary structure composed of at least 40% of telomeric G-quadruplex tetramer type, said oligonucleotide being capable of balancing or increasing levels of interferons in a mammalian subject upon administration to said subject. Preferably, said tertiary type is present in at least 60%, more preferably 80%, even more preferably 90% of telomeric G-quadruplex tetramer type. Preferably, said oligonucleotide is capable of increasing levels of interferons.

In one embodiment of this aspect, said oligonucleotide comprises at least one nucleotide that has a phosphate backbone modification. Preferably, said phosphate backbone modification is a phosphorothioate or phosphorodithioate modification.

In another embodiment of this aspect, said oligonucleotide comprises of about 8 to about 120 nucleotides, preferably of about 12 to about 30 nucleotides.

In another embodiment of this aspect, said interferon represents interferon-α, interferon-β and/or interferon-γ.

In another embodiment of this aspect, said oligonucleotide is selected from the group consisting of SEQ ID NOs 60, 62, 67, 68, 70, 72, 74-77 and 79-80.

In another embodiment of this aspect, said oligonucleotide is selected from the group consisting of SEQ ID NOs 76, 77 and 80.

In another embodiment of this aspect, there is provided said oligonucleotide for use in therapy.

In another embodiment of this aspect, there is provided said oligonucleotide for use in treating a disease where balancing or increasing the levels of interferons are beneficial for said treatment. Typically, said oligonucleotide for use in treating a disease is capable of where increasing the levels of interferons.

In another embodiment of this aspect, there is provided said oligonucleotide for use in the treatment of diseases selected from infectious diseases, inflammatory diseases, neurodegenerative diseases and cancer.

In another embodiment of this aspect, there is provided said oligonucleotide for use in the treatment of diseases selected from inflammatory bowel disease, hairy cell leukemia, haematological malignancy, multiple sclerosis, hepatitis B, hepatitis C, chronic hepatitis, cirrhosis, chronic granulomatosis disease and severe malignant osteopetrosis.

In another embodiment of this aspect, there is provided use of said oligonucleotide, in the preparation of a medicament useful in the treatment where increasing or balancing the levels of interferons are beneficial for said treatment. Preferably, said oligonucleotide is capable of increasing the levels of interferons.

In another embodiment of this aspect, there is provided use of said oligonucleotide, in the preparation of a medicament useful in the treatment of infectious diseases, inflammatory diseases, neurodegenerative diseases or cancer.

In another embodiment of this aspect, there is provided use of said oligonucleotide, in the preparation of a medicament useful in the treatment of a disease selected from inflammatory bowel disease, hairy cell leukemia, haematological malignancy, multiple sclerosis, hepatitis B, hepatitis C, chronic hepatitis, cirrhosis, chronic granulomatosis disease and severe malignant osteopetrosis.

In another embodiment of this aspect, there is provided use of said oligonucleotide, which use further comprises one or more additional agents effective in treating infectious diseases, inflammatory diseases, neurodegenerative diseases or cancer.

In another embodiment of this aspect, there is provided a method of treating a disease wherein increasing or balancing the levels of interferons are beneficial for said treatment, comprising administering to a subject in need thereof, of said oligonucleotide. Preferably, said oligonucleotide is capable of increasing the levels of interferons.

In another embodiment of this aspect, there is provided a method of treating infectious diseases, inflammatory diseases, neurodegenerative diseases or cancer, comprising administering to a subject in need thereof, of said oligonucleotide.

In another embodiment of this aspect, there is provided a method of treating a disease selected from inflammatory bowel disease, hairy cell leukemia, haematological malignancy, multiple sclerosis, hepatitis B, hepatitis C, chronic hepatitis, cirrhosis, chronic granulomatosis disease and severe malignant osteopetrosis, comprising administering to a subject in need thereof, of said oligonucleotide.

In another embodiment of this aspect, there is provided a method of treating said disease or diseases, in combination with one or more additional agents effective in treating infectious diseases, inflammatory diseases, neurodegenerative diseases or cancer.

In another aspect of the invention, there is provided a pharmaceutical composition comprising an oligonucleotide of the invention as well as further oligonucleotides identifiable by the methods of the invention, together with pharmaceutically acceptable adjuvants, diluents or carriers.

According to an embodiment, said oligonucleotide is administered in an amount of about 1 to about 2000 micro g per kg body weight, preferably about 1 to about 1000 micro g per kg body weight. Most preferably the oligonucleotide is administered in an amount of about 1 to 500 micro g per kg body weight.

According to another embodiment, said oligonucleotide is administered in a sufficient amount to induce immunomodulation.

In a method according to the invention, the route of administration is chosen from mucosal, subcutaneous, intramuscular, intravenous and intraperitoneal administration. According to an embodiment of the method, the mucosal administration is selected from nasal, oral, gastric, ocular, rectal, colonic, urogenital and vaginal administration.

Nasal administration constitutes one embodiment of the method according to the invention. There are several methods and devices available for nasal administration; single or multi-dosing of both liquid and powder formulations, with either topical or systemic action. Using appropriate devices or administration techniques, it is possible to target the olfactory bulb region for delivery to the CNS. The present invention is not limited to particular methods or devices for administering the oligonucleotides to the nasal mucous membrane. The initial animal studies have shown that simple instillation by pipette works satisfactorily, although for human use, devices for reliable single or multi dose of administration would be preferred.

According to another embodiment of the invention, the oligonucleotides are administered to the mucous membrane of the colon through rectal instillation, e.g. in the form of an aqueous enema comprising the oligonucleotides suspended in water or a suitable buffer.

According to another embodiment of the invention, the oligonucleotides are administered to the mucous membrane of the lungs or the airways through inhalation of an aerosol, comprising the oligonucleotides suspended in a suitable buffer, or by performing a lavage, also comprising the oligonucleotides suspended in water or a suitable buffer.

According to yet another embodiment of the invention, the oligonucleotides are administered to the mucous membrane of the urogenital tract, such as the urethra, the vagina etc through application of a solution, a buffer, a gel, salve, paste or the like, comprising the oligonucleotides suspended in water or in a suitable vehicle.

A particular embodiment involves the use of an oligonucleotide according to the invention for use in conjunction with the administration of an anti cell surface marker antibody such as Rituximab. There are indications that oligonucleotides according to the invention can induce the expression of cells surface markers, such as on immune cells such as CD20 on B cells, and thereby enhance the rate of apoptosis in human B-cells mediated by monoclonal antibodies directed against CD20 (such as rituximab). The inventors thus make available a combination therapy involving the use of oligonucleotide compounds together with an anti cell surface marker antibody.

A particular embodiment involves the use of an oligonucleotide according to the invention for use in conjunction with the administration of glucocorticosteroids (GCS). There are indications that the oligonucleotides according to the invention can enhance GCS action. The inventors thus make available a combination therapy involving the use of oligonucleotide compounds together with a GCS. This is contemplated to be able to reduce GCS consumption, and thereby reduce the cost, side-effects and risks associated with the said GCS therapy. Consequently, in this embodiment, said compound is administered together with a GCS.

A skilled person is well aware of the fact that there are several approaches to the treatment of inflammatory and/or autoimmune diseases. Naturally new approaches are constantly being developed, and it is conceived that the oligonucleotides, their use and methods of treatment according to the present invention, will find utility also in combination with future treatments. The inventors presently believe that the inventive oligonucleotides, their use and methods of treatment would be useful as a stand-alone therapy for inflammatory and/or autoimmune diseases. It cannot however be excluded that the inventive oligonucleotides will have utility in combination with existing or future treatment therapies for these diseases.

The oligonucleotide is administered in a therapeutically effective amount. The definition of a "therapeutically effective dose" or "therapeutically effective amount" is dependent on the disease and treatment setting, a "therapeutically effective amount" being a dose which alone or in combination with other treatments results in a measurable improvement of the patient's condition. A skilled person can determine a therapeutically effective amount either empirically, or based on laboratory experiments, performed without undue burden. The treating physician can also determine a suitable amount, based on his/her experience and considering the nature and severity of the disease, as well as the patient's condition.

Another embodiment is the administration of the oligonucleotide in two or three or more separate amounts, separated in time by about 12 hours, about 24 hours, about 48 hours, about one week and about 4 weeks. Another embodiment is the administration of the oligonucleotide prior, in parallel or after the administration of a combination therapy.

The embodiments of the invention have many advantages. So far, the administration of an oligonucleotide in the amounts defined by the inventors has not elicited any noticeable side-effects. Further, the mucosal administration is easy, fast, and painless, and surprisingly results in a systemic effect. It is held that this effect, either alone, or in combination with existing and future treatments, offers a promising approach to fight the diseases of interest.

In another aspect of the invention, the oligonucleotides of the invention are useful for steroid re-sensitization.

In another aspect of the invention, the oligonucleotides of the invention are useful to influence the properties and behaviour of polymorphonuclear cells, in particular the recruitment and/or migration of polymorphonuclear cells to a site of inflammation, and that they through this mechanism have utility in the prevention, treatment and/or alleviation of various diseases such as ischemia.

SEQ ID NOs 12, 36-42, 46, 52, 55, 58, 61, 63-66, 69, 71, 73, 86-88 and 92-93 are included in the sequence listing to provide comparative oligonucleotide sequences.

EXAMPLES

Example 1

Figure 4A:
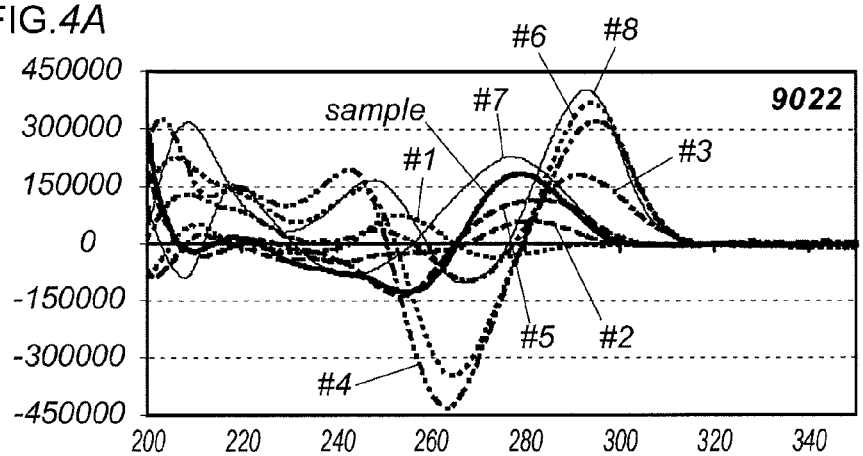
Figure 4B:
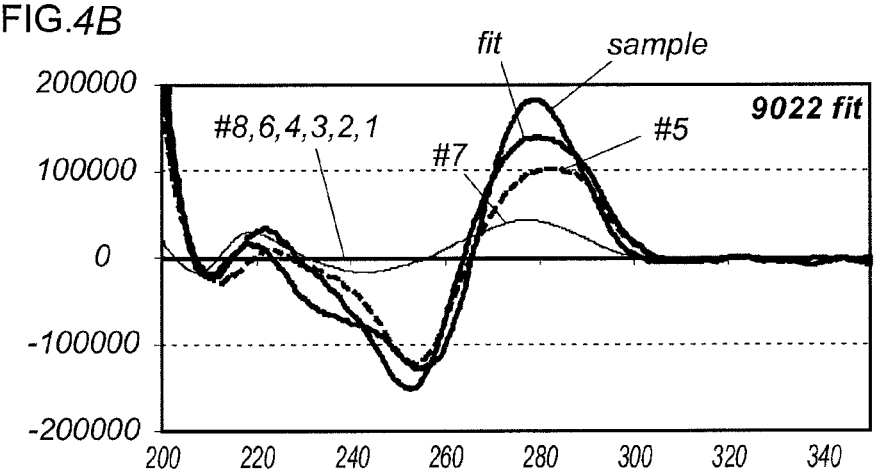
Figure 5A:
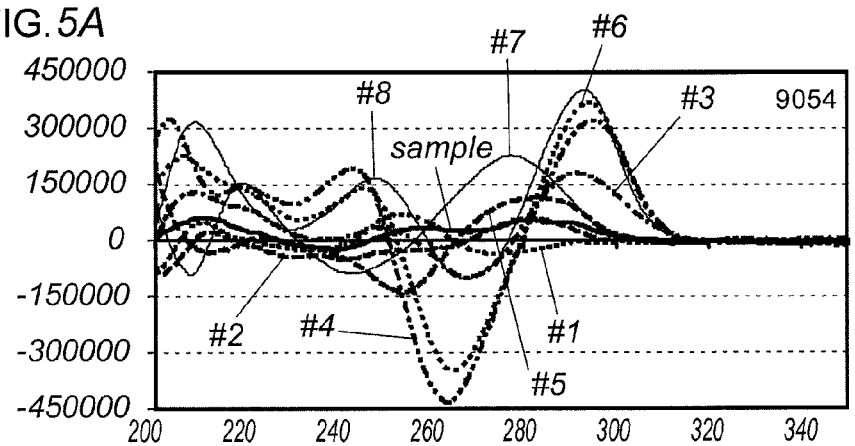
Figure 5B:
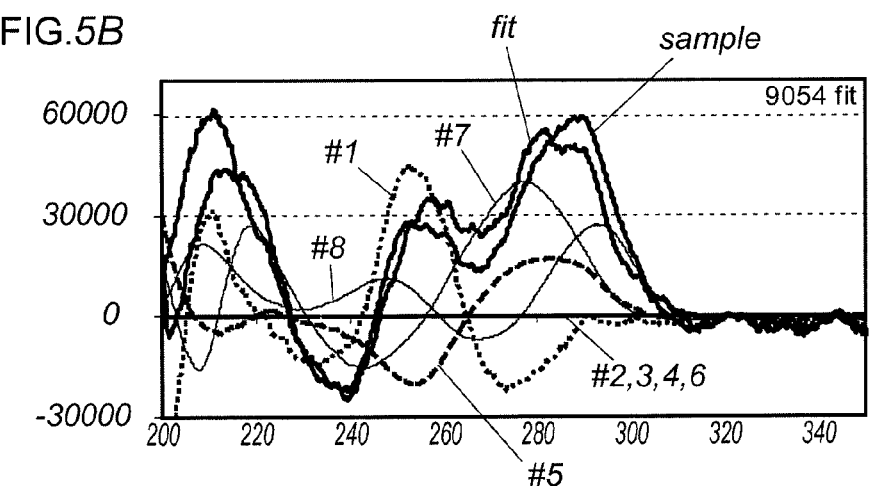
Figure 6A:
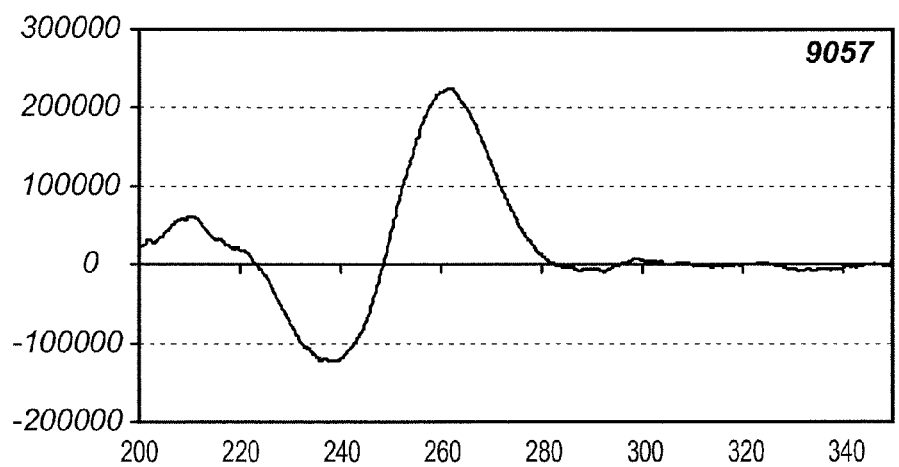
FIG. 6A represents the molar ellipticity of IDX 9057 (SEQ ID NO 77) with major contribution (64.0%) of telomeric G-quadruplex tetramer type of tertiary structure, which oligonucleotide is linked dominantly with IFN induction.
Figure 6B:
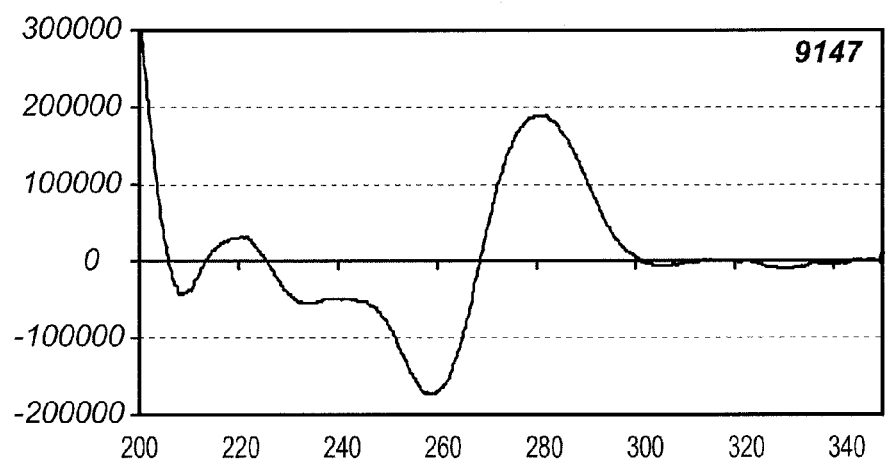
FIG. 6B represents the molar ellipticity of IDX 9147 (SEQ ID NO 33) with major contribution (97.0%) of non-G-quadruplex dimer type of tertiary structure, which oligonucleotide is linked dominantly with IL-6/IL-10 induction.

Relative Structural Composition of CD Spectra of Oligonucleotides of the Invention The fits of the CD spectra of eight reference oligonucleotides (Table 1 and FIG. 1) overlaid on the measured CD spectra of selected oligonucleotides of the invention are presented in FIG. 4. The tertiary, structural properties of the reference oligonucleotides were analyzed by circular dichroism (CD) measurement and the resulting traces are presented in FIG. 1. Prior to the CD measurements the oligonucleotide samples were annealed by heating to 90° C. and then slow cooled in water bath to room temperature (20° C.) over a period of 8 h. Selected oligonucleotides were annealed by heating to 90° C. and then snap-cooled in ice-cold water bath at 4° C. and then brought to room temperature. CD measurements in UV range were conducted on a Jasco J-720 spectropolarimeter (Jasco Corp., Tokyo, Japan). For the measurement 300 µl of the samples was loaded into a quartz cuvette with 0.1 cm path length (total volume 400 µl). The CD spectra of the oligonucleotide samples used for the calculation were collected at 20 µM concentration of the oligonucleotide. The CD measurements were conducted at the rate of 100 nm/min with 4 sec response time. Seven sequential spectra were taken for each sample with the final spectrum being the average of the 7 consecutive measurements. CD spectra of oligonucleotide samples were measured in 1×PBS buffer (10 mM phosphate buffer (pH 7.4) with 140 mM NaCl and 27 mM KCl). The blank spectrum of 1×PBS was subtracted from the CD spectra of the samples solutions.

CD spectra were collected in the range from 190 to 350 nm at 25° C. for all samples. The temperature in the sample holder was controlled and kept constant (±0.1° C.) with the help of a Peltier element (PTC-348 WI). Data collection and evaluation were carried out by the software supplied with the instrument. The resulting spectra were normalized to the concentration of the oligonucleotide and zeroed at 320 nm.

For better visualization and analysis of the tertiary structure of oligonucleotides of the invention, a custom-built computer program was used to calculate the relative composition of the CD spectra. The program was written in MatLab (Mathworks Corp.). The algorithm is based on the assumption that the samples spectra are the linear combinations of the references spectra (FIG. 1). The fitting of the experimental data were performed following Levenberg-Marquart non-linear least-squares algorithm. Only the data collected at high tension signal below approx. 600 V were considered reliable. Only the spectra measured in wavelength window from 200 to 350 nm have been included in the calculations of the relative structural composition of oligonucleotide samples.

Example 2

Method for Determination of Oligonucleotide-Stimulated Cytokine Production Profile of Healthy Individuals Represented by Cultured Peripheral Blood Mononuclear Cells (PBMC)

PBMC Isolation, Stimulation and Cultivation

Buffy coats from healthy blood donors were obtained from the Karolinska University blood bank and used for preparation of peripheral blood mononuclear cells (PBMC). PBMC were isolated by density centrifugation on Ficoll Paque (Amersham Biosciences AB, Uppsala, Sweden). The cells were then further washed in PBS, and the viability and the cell number were determined by counting the cells in Trypan blue (Sigma Aldrich, Stockholm, Sweden). Thereafter the cells were re-suspended in complete cell medium consisting of RPMI 1640 (Sigma Aldrich) supplemented with 10% heat inactivated fetal calf serum (FCS, Invitrogen), 2 mM L-glutamine, 100 U/mL penicillin, 100 μg/mL streptomycin, 10 mM HEPES (Sigma Aldrich) and 5 μg/mL gentamicin (Invitrogen). The PBMC were cultured in 48-well culture tissue plates (Becton Dickinson, Franklin Lakes, N.J.) at a concentration of $5\times10^6$ cells/mL with 10 μM of oligonucleotides of the invention, with medium alone as a negative control in a total volume of 400 μl/well. The cells were incubated for 48 h at 37° C. in a humidified cell culture incubator (Thermo Scientific, Waltham, Mass.) with 5% $CO_2$, in air, after which the culture supernatants were collected and frozen at −20° C. for later cytokine analysis.

Cytometric Bead Array Measurements and Data Analysis

Culture supernatants from PBMC stimulated with oligonucleotides of the invention were analyzed for the presence of the cytokines IFN-γ, IL-6, and IL-10 using cytometric bead array flex kit (Becton Dickinson) according to the manufacturer's instructions on a FACSArray flow cytometer (Becton Dickinson). The data were analyzed using FCAP Array software (Becton Dickinson).

ELISA and Data Analysis

Culture supernatants from PBMC stimulated with oligonucleotides of the invention were analyzed for the presence of IFN-α using human IFN-α Multi-subtype ELISA kit (PBL, Biomedical Laboratories, NJ, USA) and IFN-β was detected with human IFN-β ELISA kit (Fujirebio INC. Tokyo, Japan) according to the manufacturer's instructions. The absorbance was measured on a microplate reader (Tecan, Männedorf, Switzerland) and the data were analyzed using Magellan software (Tecan). One set of results are shown in Table 6, which shows Cytometric Bead Array (CBA) mean data (IL6, IL10, IFN-γ) from four healthy individuals and ELISA mean data (IFN-α, IFN-β) from six healthy individuals on cytokines and interferons production of PBMC cultured in presence of selected oligonucleotides of the invention.

TABLE 6

Induction of cytokines by oligonucleotides with different contributions of non-G-quadruplex dimer type of tertiary structure.

| SEQ ID NO | IDX-no | IL-6 | IL-10 | IFN-α | IFN-β | IFN-γ |
|---|---|---|---|---|---|---|
| 7  | 9011 | — | — | 1 | — | — |
| 59 | 0465 | 1 | — | — | — | — |
| 31 | 9153 | — | — | — | — | — |
| 32 | 9146 | — | — | 1 | — | — |
| 43 | 0495 | — | — | — | — | — |
| 44 | 9022 | 4 | 4 | 1 | — | — |
| 10 | 0475 | 3 | 3 | 1 | — | — |
| 11 | 0480 | 2 | 3 | — | — | — |
| 45 | 9012 | 3 | 5 | — | — | — |
| 57 | 0912 | 2 | 3 | — | — | — |
| 47 | 9071 | 4 | 4 | — | — | — |
| 48 | 0001 | 4 | 3 | 5 | 2 | — |
| 49 | 9024 | 3 | 4 | — | — | — |
| 50 | 9038 | 5 | 4 | 5 | — | 1 |
| 13 | 9013 | 3 | 4 | — | — | — |
| 14 | 9014 | 3 | 4 | — | — | — |
| 15 | 9017 | 4 | 4 | 3 | — | — |
| 16 | 9028 | 4 | 4 | 1 | — | 1 |
| 17 | 9029 | 4 | 3 | 2 | — | — |
| 18 | 9069 | 3 | 4 | — | — | — |
| 19 | 9070 | 3 | 4 | — | — | — |
| 20 | 9072 | 3 | 4 | — | — | — |
| 21 | 9073 | 3 | 4 | — | — | — |
| 51 | 9074 | 3 | 5 | — | — | — |
| 22 | 9091 | 3 | 4 | — | — | — |
| 53 | 9092 | 3 | 4 | — | — | — |
| 54 | 9095 | 3 | 4 | — | — | — |
| 23 | 9100 | 4 | 3 | — | — | — |
| 56 | 0910 | 3 | 3 | — | — | — |
| 24 | 9138 | 5 | 4 | 2 | 1 | 1 |
| 25 | 9139 | 4 | 3 | 4 | 1 | 1 |
| 26 | 9140 | 3 | 3 | 2 | 1 | 1 |
| 27 | 9141 | 5 | 3 | 3 | 1 | 1 |
| 28 | 9142 | 4 | 3 | 2 | — | 1 |
| 29 | 9143 | 4 | 3 | 3 | 1 | 1 |
| 30 | 9144 | 5 | 4 | 3 | — | 1 |
| 33 | 9147 | 4 | 3 | — | — | 1 |
| 34 | 9148 | 4 | 3 | 3 | — | 1 |
| 35 | 9149 | 5 | 3 | 3 | — | 2 |

The mean concentration (pg/ml) of IFN-α and IFN-β is scored as follows; [−]<125; 125≤[1]<250; 250≤[2]<500; 500≤[3]<750; 750≤[4]<1000; and 1000≤[5]

The mean concentration (pg/ml) of IL6, IL10 and IFN-γ is scored as follows; [−]<65; 65≤[1]<125; 125≤[2]<250; 250≤[3]<500; 500≤[4]<750; and 750≤[5]

Another set of results are shown in Table 7, which shows Cytometric Bead Array (CBA) mean data (IL6, IL10, IFN-γ) from four healthy individuals and ELISA mean data (IFN-α, IFN-β) from six healthy individuals on cytokines and interferons production of PBMC cultured in presence of selected oligonucleotides of the invention.

TABLE 7

Induction of cytokines by oligonucleotides with different contributions of telomeric G-quadruplex tetramer type of tertiary structure.

| SEQ ID No | IDX-No | IL6 | IL10 | IFN-α | IFN-β | IFN-γ |
|---|---|---|---|---|---|---|
| 59 | 0465 | 2 | 1 | — | — | — |
| 91 | 0445 | — | — | — | — | — |
| 31 | 9153 | — | — | — | — | — |
| 32 | 9146 | — | — | 1 | — | — |
| 43 | 0495 | 2 | 1 | — | — | — |
| 94 | 9134 | — | — | — | — | — |
| 7  | 9011 | — | — | 1 | — | — |
| 81 | 9054 | 3 | 2 | 5 | 5 | 1 |
| 83 | 9059 | 5 | 4 | 5 | 5 | 1 |
| 80 | 9133 | 3 | 3 | 3 | — | — |
| 84 | 9004 | 3 | 2 | 5 | 3 | 1 |
| 85 | 9005 | 2 | 2 | 5 | 5 | 1 |
| 60 | 9008 | 2 | 3 | 5 | 1 | 1 |
| 62 | 9019 | 1 | 2 | 5 | 2 | — |
| 67 | 9027 | 3 | 3 | 5 | 2 | — |
| 68 | 9039 | 2 | 2 | 4 | — | 1 |
| 70 | 9041 | 4 | 3 | 5 | 1 | 1 |
| 72 | 9047 | 2 | 2 | 5 | 2 | 1 |
| 74 | 9049 | 3 | 4 | 5 | — | 1 |
| 75 | 9050 | 2 | 3 | 5 | 2 | 1 |
| 76 | 9055 | 4 | 3 | 5 | 5 | 2 |
| 77 | 9057 | 3 | 3 | 5 | 5 | 1 |

TABLE 7-continued

Induction of cytokines by oligonucleotides with different contributions of telomeric G-quadruplex tetramer type of tertiary structure.

| SEQ ID No | IDX-No | IL6 | IL10 | IFN-α | IFN-β | IFN-γ |
|---|---|---|---|---|---|---|
| 78 | 9067 | 4 | 2 | 5 | 1 | — |
| 79 | 9068 | 1 | 1 | 5 | 2 | — |
| 89 | 9053 | 5 | 3 | 5 | 1 | 1 |
| 90 | 9058 | 5 | 4 | 5 | 5 | 1 |

The mean concentration (pg/ml) of IFN-α and IFN-β is scored as follows; [−]<125; 125≤[1]<250; 250≤[2]<500; 500≤[3]<750; 750≤[4]<1000; and 1000≤[5]

The mean concentration (pg/ml) of IL6, IL10 and IFN-γ is scored as follows; [−]<65; 65≤[1]<125; 125≤[2]<250; 250≤[3]<500; 500≤[4]<750; and 750≤[5]

Example 3

Relation Between Tertiary Structure of Inventive Compounds and their Biological Activity The relative composition of tertiary structure of representative oligonucleotides of the invention, compared their ability to induce specific cytokines, are shown in Table 8.

TABLE 8

Non-G-quadruplex dimer type contribution linked dominantly with IL-6/IL-10 induction.

| SEQ ID NO | IDX- No | % contribution of REF #5 (non-G-quadruplex dimer) | % contribution of REF #7 (random) | % contribution of other REFs | ILs | | IFNs | | |
|---|---|---|---|---|---|---|---|---|---|
| | | | | | 6 | 10 | α | β | γ |
| 7 | 9011 | 0.0 | 100.0 | 0.0 | − | − | − | − | − |
| 31 | 9153 | 14.5 | 85.5 | 0.0 | − | − | − | − | − |
| 32 | 9146 | 0.0 | 98.7 | 1.3 | − | − | − | − | − |
| 59 | 0465 | 28.0 | 5.2 | 66.8 | − | − | − | − | − |
| 43 | 0495 | 0.0 | 100.0 | 0.0 | − | − | − | − | − |
| 44 | 9022 | 91.6 | 8.4 | 0.0 | ‡ | + | − | − | − |
| 10 | 0475 | 53.6 | 46.4 | 0.0 | ‡ | (+) | − | − | − |
| 11 | 0480 | 81.4 | 17.8 | 0.0 | (+) | (+) | − | − | − |
| 57 | 0912 | 72.2 | 27.8 | 0.0 | (+) | + | − | − | − |
| 47 | 9071 | 60.2 | 39.2 | 0.6 | ‡ | ‡ | − | − | − |
| 48 | 0001 | 64.0 | 36.0 | 0.0 | ‡ | + | − | − | − |
| 49 | 9024 | 83.1 | 16.9 | 0.0 | + | ‡ | − | − | − |
| 16 | 9028 | 74.2 | 24.2 | 1.6 | ‡ | ‡ | − | − | (+) |
| 33 | 9147 | 97.0 | 0.0 | 3.0 | ‡ | + | − | − | (+) |
| 28 | 9142 | 94.7 | 0.0 | 5.3 | ‡ | + | − | − | (+) |

The mean concentration (pg/ml) of IL6 and IL10 is scored as follows; [−]<125; 125≤[(+)]<350; 350≤[+]<500, 500≤[‡]

The mean concentration (pg/ml) of IFN-γ is scored as follows; [−]<60; 60≤[(+)]<100; 100≤[+]

The data in Table 8 shows that representative oligonucleotides that are present in at least 45% non-G-quadruplex dimer type (related to Ref #5, SEQ ID NO 5) are capable of increasing levels of cytokines IL-6 and IL-10. The data (IL-6, IL-10, IFN-α, IFN-β and IFN-γ) are obtained in accordance with the methods set out in Example 1. The tertiary structure of SEQ ID NO 7, SEQ ID NO 31, SEQ ID NO 32, SEQ ID NO 43 and SEQ ID NO 59 (Tables 6 and 8) represents less than 45% non-G-quadruplex dimer type and, thus, according to the invention, are not capable of sufficiently increasing levels of cytokines IL-6 and IL-10.

The relative composition of tertiary structure of further representative oligonucleotides of the invention, compared with their ability to induce specific cytokines, are shown in Table 9.

TABLE 9

Telomeric G-quadruplex tetramer type contribution linked dominantly with IFN induction.

| SEQ ID NO | IDX- No | % contribution of REF #1 (telomeric G-quadruplex tetramer) | % contribution of REF #2 (fragile X G-quadruplex dimer) | % contribution of REF #5 (non-G-quadruplex dimer) | % contribution of REF #7 (random) | % Contribution of other REFs | IL | | IFN | | |
|---|---|---|---|---|---|---|---|---|---|---|---|
| | | | | | | | 6 | 10 | α | β | γ |
| 7 | 9011 | 0.0 | 0.0 | 0.0 | 100.0 | 0.0 | − | − | − | − | − |
| 32 | 9146 | 0.0 | 0.0 | 0.0 | 98.7 | 1.3 | − | − | − | − | − |
| 43 | 0495 | 0.0 | 0.0 | 0.0 | 100.0 | 0.0 | − | − | − | − | − |
| 91 | 0445 | 15.3 | 0.0 | 0.0 | 49.1 | 35.6 | − | − | − | − | − |
| 59 | 0465 | 22.2 | 35.4 | 28.0 | 5.2 | 5.0 | − | − | − | − | − |
| 94 | 9134 | 25.4 | 41.7 | 6.0 | 22.7 | 4.1 | − | − | − | − | − |
| 81 | 9054 | 61.0 | 0.0 | 14.8 | 17.5 | 7.7 | (+) | (+) | ‡ | + | (+) |
| 83 | 9059 | 49.0 | 0.0 | 0.0 | 43.2 | 7.8 | ‡ | ‡ | ‡ | + | (+) |
| 80 | 9133 | 44.3 | 0.0 | 10.1 | 43.8 | 1.8 | (+) | + | (+) | − | − |
| 76 | 9055 | 90.0 | 0.0 | 0.0 | 10.0 | 0.0 | ‡ | + | ‡ | + | + |
| 77 | 9057 | 64.0 | 0.0 | 0.0 | 36.0 | 0.0 | + | (+) | ‡ | + | (+) |

The mean concentration (pg/ml) of IFN-α and IFN-β is scored as follows: [−]<500; 500≤[(+)]<1000; 1000≤[+]<5000; 5000≤[‡]

The mean concentration (pg/ml) of IL6 and IL10 is scored as follows; [−]<125; 125≤[(+)]<350; 350≤[+]<500; 500≤[‡]

The mean concentration (pg/ml) of IFN-γ is scored as follows; [−]<60; 60≤[(+)]<100; 100≤[+]

The data in Table 9 shows that representative oligonucleotides that are present in at least 40% telomeric G-quadruplex tetramer type (related to Ref #1, SEQ ID NO 1) are capable of increasing levels of interferons. The data (IL-6, IL-10, IFN-α, IFN-β and IFN-γ) are obtained in accordance with the methods set out in Example 1. The tertiary structure of SEQ ID NO 59, SEQ ID NO 91, SEQ ID NO 31, SEQ ID NO 32, SEQ ID NO 43, SEQ ID NO 94 and SEQ ID NO 7 (Tables 7, and 9) represents less than 40% telomeric G-quadruplex tetramer type and, thus, according to the invention, are not capable of increasing levels of interferons.

---

The invention claimed is:

1. An oligonucleotide, identifiable by a method comprising analyzing which tertiary structure type said oligonucleotide adopts in phosphate-buffered saline solution, wherein the oligonucleotide is selected from the group consisting of SEQ ID NOs: 13-16, 68, 70 and 79.

2. An oligonucleotide selected from the group consisting of SEQ ID NOs 13-16.

3. An oligonucleotide selected from the group consisting of SEQ ID NOs 68, 70, and 79.

4. The oligonucleotide according to claim 2, comprising of about 8 to about 120 nucleotides.

5. A method for treating a disease, comprising administering an effective amount of an oligonucleotide selected from the group consisting of SEQ ID NOs: 13-16, 68, 70 and 79, to a subject in need thereof, wherein an increase or balancing the levels of cytokines is beneficial to said disease.

6. The oligonucleotide according to claim 4, comprising of about 12 to about 30 nucleotides.

7. The method for treating a disease of claim 5, wherein the disease is selected from the group consisting of inflammatory bowel disease, meningitis, allergy, atopic eczema, asthma, COPD, infectious diseases, inflammatory diseases, neurodegenerative diseases, cancer, hairy cell leukemia, haematological malignancy, multiple sclerosis, hepatitis B, hepatitis C, chronic hepatitis, cirrhosis, chronic granulomatosis disease, malignant osteopetrosis, and combinations thereof.

8. The oligonucleotide of claim 2, wherein the oligonucleotide has at least one nucleotide that has a phosphate backbone modification, wherein the phosphate backbone modification is phosphorothioate or phosphorodithioate modification.

9. The oligonucleotide of claim 8, wherein the oligonucleotide SEQ ID NO: 13 has a phosphorothioate modification at positions 1, 2, 3, 24, 25, and 26 of SEQ ID NO: 13.

10. The oligonucleotide of claim 8, wherein the oligonucleotide SEQ ID NO: 14 has a phosphorothioate modification at positions 1, 2, 3, 25, 26, and 27 of SEQ ID NO: 14.

11. The oligonucleotide of claim 8, wherein the oligonucleotide is SEQ ID NO: 15 has a phosphorothioate modification at positions 1, 2, 3, 20, 21, and 22 of SEQ ID NO: 15.

12. The oligonucleotide of claim 8, wherein the oligonucleotide is SEQ ID NO: 16 has a phosphorothioate modification at positions 1, 2, 3, 18, 19, and 20 of SEQ ID NO: 16.

13. The oligonucleotide of claim 3, wherein the oligonucleotide has at least one nucleotide that has a phosphate backbone modification, wherein the phosphate backbone modification is phosphorothioate or phosphorodithioate modification.

14. The oligonucleotide of claim 13, wherein the oligonucleotide is SEQ ID NO: 68 has a phosphorothioate modification at positions 1, 2, 3, 20, 21, and 22 of SEQ ID NO: 68.

15. The oligonucleotide of claim 13, wherein the oligonucleotide is SEQ ID NO: 70 has a phosphorothioate modification at positions 1, 2, 3, 21, 22, and 23 of SEQ ID NO: 70.

16. The oligonucleotide of claim 13, wherein the oligonucleotide is SEQ ID NO: 79 has a phosphorothioate modification at positions 1, 2, 3, 18, 19, and 20 of SEQ ID NO: 79.

* * * * *

SEQUENCE LISTING

```
<160> NUMBER OF SEQ ID NOS: 94

<210> SEQ ID NO 1
<211> LENGTH: 6
<212> TYPE: DNA
<213> ORGANISM: Artificial Sequence
<220> FEATURE:
<223> OTHER INFORMATION: IDX-0400

<400> SEQUENCE: 1 tggggt                                                                    6

<210> SEQ ID NO 2
<211> LENGTH: 11
<212> TYPE: DNA
<213> ORGANISM: Artificial Sequence
<220> FEATURE:
<223> OTHER INFORMATION: IDX-0405

<400> SEQUENCE: 2
gcggtttgcg g                                                             11

<210> SEQ ID NO 3
<211> LENGTH: 10
<212> TYPE: DNA
<213> ORGANISM: Artificial Sequence
<220> FEATURE:
<223> OTHER INFORMATION: IDX-0415

<400> SEQUENCE: 3
gggttttggg                                                               10

<210> SEQ ID NO 4
<211> LENGTH: 12
<212> TYPE: DNA
<213> ORGANISM: Artificial Sequence
<220> FEATURE:
<223> OTHER INFORMATION: IDX-0420

<400> SEQUENCE: 4
ggggttttgg gg                                                            12

<210> SEQ ID NO 5
<211> LENGTH: 7
<212> TYPE: DNA
<213> ORGANISM: Artificial Sequence
<220> FEATURE:
<223> OTHER INFORMATION: IDX-0430

<400> SEQUENCE: 5 gcatgct                                                                   7

<210> SEQ ID NO 6
<211> LENGTH: 20
```

```
<212> TYPE: DNA
<213> ORGANISM: Artificial Sequence
<220> FEATURE:
<223> OTHER INFORMATION: IDX-0435

<400> SEQUENCE: 6
ggttttggtt ttggttttgg                                               20

<210> SEQ ID NO 7
<211> LENGTH: 18
<212> TYPE: DNA
<213> ORGANISM: Artificial Sequence
<220> FEATURE:
<223> OTHER INFORMATION: IDX-9011
<220> FEATURE:
<221> NAME/KEY: misc_feature
<222> LOCATION: (1)..(18)
<223> OTHER INFORMATION: * indicates phosphorothioate modification in
      T*C*A*CGACCGTCAAAC*T*C*C

<400> SEQUENCE: 7
tcacgaccgt caaactcc                                                 18

<210> SEQ ID NO 8
<211> LENGTH: 15
<212> TYPE: DNA
<213> ORGANISM: Artificial Sequence
<220> FEATURE:
<223> OTHER INFORMATION: IDX-0410

<400> SEQUENCE: 8
ggttggtgtg gttgg                                                    15

<210> SEQ ID NO 9
<211> LENGTH: 22
<212> TYPE: DNA
<213> ORGANISM: Artificial Sequence
<220> FEATURE:
<223> OTHER INFORMATION: IDX-0470

<400> SEQUENCE: 9
tcgtcgttct gccatcgtcg tt                                            22

<210> SEQ ID NO 10
<211> LENGTH: 22
<212> TYPE: DNA
<213> ORGANISM: Artificial Sequence
<220> FEATURE:
<223> OTHER INFORMATION: IDX-0475
<220> FEATURE:
<221> NAME/KEY: misc_feature
<222> LOCATION: (1)..(22)
<223> OTHER INFORMATION: * indicates phosphorothioate modification in
      T*T*G*TTGTTCTGCCATCGTC*G*T*T

<400> SEQUENCE: 10
ttgttgttct gccatcgtcg tt                                            22

<210> SEQ ID NO 11
<211> LENGTH: 22
<212> TYPE: DNA
<213> ORGANISM: Artificial Sequence
<220> FEATURE:
<223> OTHER INFORMATION: IDX-0480
<220> FEATURE:
<221> NAME/KEY: misc_feature
<222> LOCATION: (1)..(22)
<223> OTHER INFORMATION: * indicates phosphorothioate modification in
      T*G*C*TGCTTCTGCCATGCTG*C*T*T
```

```
<400> SEQUENCE: 11
tgctgcttct gccatgctgc tt                                              22

<210> SEQ ID NO 12
<211> LENGTH: 22
<212> TYPE: DNA
<213> ORGANISM: Artificial Sequence
<220> FEATURE:
<223> OTHER INFORMATION: IDX-0485
<220> FEATURE:
<221> NAME/KEY: misc_feature
<222> LOCATION: (1)..(22)
<223> OTHER INFORMATION: * indicates phosphorothioate modification in
      T*C*G*T*C*G*T*T*C*T*G*C*C*A*T*C*G*T*C*G*T*T

<400> SEQUENCE: 12
tcgtcgttct gccatcgtcg tt                                              22

<210> SEQ ID NO 13
<211> LENGTH: 27
<212> TYPE: DNA
<213> ORGANISM: Artificial Sequence
<220> FEATURE:
<223> OTHER INFORMATION: IDX-9013
<220> FEATURE:
<221> NAME/KEY: misc_feature
<222> LOCATION: (1)..(27)
<223> OTHER INFORMATION: *indicates phosphorothioate modification in
      T*C*G*TTCGTCTTGTTCGTTTGTTCG*T*G*G

<400> SEQUENCE: 13
tcgttcgtct tgttcgtttg ttcgtgg                                         27

<210> SEQ ID NO 14
<211> LENGTH: 28
<212> TYPE: DNA
<213> ORGANISM: Artificial Sequence
<220> FEATURE:
<223> OTHER INFORMATION: IDX-9014
<220> FEATURE:
<221> NAME/KEY: misc_feature
<222> LOCATION: (1)..(28)
<223> OTHER INFORMATION: *indicates phosphorothioate modification in
      T*C*G*TTCGTCTTTTCGTTTTCGTCGG*C*G*C

<400> SEQUENCE: 14
tcgttcgtct tttcgttttc gtcggcgc                                        28

<210> SEQ ID NO 15
<211> LENGTH: 23
<212> TYPE: DNA
<213> ORGANISM: Artificial Sequence
<220> FEATURE:
<223> OTHER INFORMATION: IDX-9017
<220> FEATURE:
<221> NAME/KEY: misc_feature
<222> LOCATION: (1)..(23)
<223> OTHER INFORMATION: *indicates phosphorothioate modification in
      T*C*C*GCGTTCGTTGTTCGTCG*C*G*G

<400> SEQUENCE: 15
tccgcgttcg ttgttcgtcg cgg                                             23

<210> SEQ ID NO 16
<211> LENGTH: 21
<212> TYPE: DNA
<213> ORGANISM: Artificial Sequence
<220> FEATURE:
```

```
<223> OTHER INFORMATION: IDX-9028
<220> FEATURE:
<221> NAME/KEY: misc_feature
<222> LOCATION: (1)..(21)
<223> OTHER INFORMATION: *indicates phosphorothioate modification in
      C*G*G*CGCGCCGTTCGTCGA*T*G*G

<400> SEQUENCE: 16
cggcgcgccg ttcgtcgatg g                                              21

<210> SEQ ID NO 17
<211> LENGTH: 19
<212> TYPE: DNA
<213> ORGANISM: Artificial Sequence
<220> FEATURE:
<223> OTHER INFORMATION: IDX-9029
<220> FEATURE:
<221> NAME/KEY: misc_feature
<222> LOCATION: (1)..(19)
<223> OTHER INFORMATION: *indicates phosphorothioate modification in
      C*G*G*CGCCGTTCGTCGA*T*G*G

<400> SEQUENCE: 17
cggcgccgtt cgtcgatgg                                                 19

<210> SEQ ID NO 18
<211> LENGTH: 26
<212> TYPE: DNA
<213> ORGANISM: Artificial Sequence
<220> FEATURE:
<223> OTHER INFORMATION: IDX-9069
<220> FEATURE:
<221> NAME/KEY: misc_feature
<222> LOCATION: (1)..(26)
<223> OTHER INFORMATION: *indicates phosphorothioate modification in
      T*C*G*TCTGCTTGTTCGTCTTGTTC*G*T*C

<400> SEQUENCE: 18
tcgtctgctt gttcgtcttg ttcgtc                                         26

<210> SEQ ID NO 19
<211> LENGTH: 30
<212> TYPE: DNA
<213> ORGANISM: Artificial Sequence
<220> FEATURE:
<223> OTHER INFORMATION: IDX-9070
<220> FEATURE:
<221> NAME/KEY: misc_feature
<222> LOCATION: (1)..(30)
<223> OTHER INFORMATION: *indicates phosphorothioate modification in
      T*C*G*TTCGTCTGCTTGTTCGTCTTGTTC*G*T*C

<400> SEQUENCE: 19
tcgttcgtct gcttgttcgt cttgttcgtc                                     30

<210> SEQ ID NO 20
<211> LENGTH: 24
<212> TYPE: DNA
<213> ORGANISM: Artificial Sequence
<220> FEATURE:
<223> OTHER INFORMATION: IDX-9072
<220> FEATURE:
<221> NAME/KEY: misc_feature
<222> LOCATION: (1)..(24)
<223> OTHER INFORMATION: *indicates phosphorothioate modification in
      T*C*G*TTCGTCTTGTTCGTCGTC*T*G*C

<400> SEQUENCE: 20
tcgttcgtct tgttcgtcgt ctgc                                           24
```

```
<210> SEQ ID NO 21
<211> LENGTH: 21
<212> TYPE: DNA
<213> ORGANISM: Artificial Sequence
<220> FEATURE:
<223> OTHER INFORMATION: IDX-9073
<220> FEATURE:
<221> NAME/KEY: misc_feature
<222> LOCATION: (1)..(21)
<223> OTHER INFORMATION: *indicates phosphorothioate modification in
      T*C*G*TTCGTCTTGTTCGTC*T*G*C

<400> SEQUENCE: 21
tcgttcgtct tgttcgtctg c                                              21

<210> SEQ ID NO 22
<211> LENGTH: 24
<212> TYPE: DNA
<213> ORGANISM: Artificial Sequence
<220> FEATURE:
<223> OTHER INFORMATION: IDX-9091
<220> FEATURE:
<221> NAME/KEY: misc_feature
<222> LOCATION: (1)..(24)
<223> OTHER INFORMATION: *indicates phosphorothioate modification in
      T*T*T*TCGTCTGCTTTCGTTTCG*T*T*T

<400> SEQUENCE: 22
ttttcgtctg ctttcgtttc gttt                                           24

<210> SEQ ID NO 23
<211> LENGTH: 23
<212> TYPE: DNA
<213> ORGANISM: Artificial Sequence
<220> FEATURE:
<223> OTHER INFORMATION: IDX-9100
<220> FEATURE:
<221> NAME/KEY: misc_feature
<222> LOCATION: (1)..(23)
<223> OTHER INFORMATION: *indicates phosphorothioate modification in
      T*G*C*C*A*T*T*C*G*T*C*G*T*T*C*T*C*G*T*C*G*T*T

<400> SEQUENCE: 23
tgccattcgt cgttctcgtc gtt                                            23

<210> SEQ ID NO 24
<211> LENGTH: 21
<212> TYPE: DNA
<213> ORGANISM: Artificial Sequence
<220> FEATURE:
<223> OTHER INFORMATION: IDX-9138
<220> FEATURE:
<221> NAME/KEY: misc_feature
<222> LOCATION: (1)..(21)
<223> OTHER INFORMATION: *indicates phosphorothioate modification in
      T*C*G*TCGTTCTGCCATCGT*C*G*T

<400> SEQUENCE: 24
tcgtcgttct gccatcgtcg t                                              21

<210> SEQ ID NO 25
<211> LENGTH: 17
<212> TYPE: DNA
<213> ORGANISM: Artificial Sequence
<220> FEATURE:
<223> OTHER INFORMATION: IDX-9139
<220> FEATURE:
<221> NAME/KEY: misc_feature
<222> LOCATION: (1)..(17)
<223> OTHER INFORMATION: *indicates phosphorothioate modification in
```

```
                       T*C*G*TCGTTCTCGTC*G*T*T

<400> SEQUENCE: 25
tcgtcgttct cgtcgtt                                                    17

<210> SEQ ID NO 26
<211> LENGTH: 16
<212> TYPE: DNA
<213> ORGANISM: Artificial Sequence
<220> FEATURE:
<223> OTHER INFORMATION: IDX-9140
<220> FEATURE:
<221> NAME/KEY: misc_feature
<222> LOCATION: (1)..(16)
<223> OTHER INFORMATION: *indicates phosphorothioate modification in
      T*C*G*TTCTGCTGAT*C*G*T

<400> SEQUENCE: 26
tcgttctgct gatcgt                                                     16

<210> SEQ ID NO 27
<211> LENGTH: 19
<212> TYPE: DNA
<213> ORGANISM: Artificial Sequence
<220> FEATURE:
<223> OTHER INFORMATION: IDX-9141
<220> FEATURE:
<221> NAME/KEY: misc_feature
<222> LOCATION: (1)..(19)
<223> OTHER INFORMATION: *indicates phosphorothioate modification in
      T*C*G*TCGTTCTGTCGTC*G*T*T

<400> SEQUENCE: 27
tcgtcgttct gtcgtcgtt                                                  19

<210> SEQ ID NO 28
<211> LENGTH: 18
<212> TYPE: DNA
<213> ORGANISM: Artificial Sequence
<220> FEATURE:
<223> OTHER INFORMATION: IDX-9142
<220> FEATURE:
<221> NAME/KEY: misc_feature
<222> LOCATION: (1)..(18)
<223> OTHER INFORMATION: *indicates phosphorothioate modification in
      T*C*G*TCGTTCGTCGTC*G*T*T

<400> SEQUENCE: 28
tcgtcgttcg tcgtcgtt                                                   18

<210> SEQ ID NO 29
<211> LENGTH: 18
<212> TYPE: DNA
<213> ORGANISM: Artificial Sequence
<220> FEATURE:
<223> OTHER INFORMATION: IDX-9143
<220> FEATURE:
<221> NAME/KEY: misc_feature
<222> LOCATION: (1)..(18)
<223> OTHER INFORMATION: *indicates phosphorothioate modification in
      T*C*G*TCGTTGCTCGTC*G*T*T

<400> SEQUENCE: 29
tcgtcgttgc tcgtcgtt                                                   18

<210> SEQ ID NO 30
<211> LENGTH: 16
<212> TYPE: DNA
<213> ORGANISM: Artificial Sequence
```

```
<220> FEATURE:
<223> OTHER INFORMATION: IDX-9144
<220> FEATURE:
<221> NAME/KEY: misc_feature
<222> LOCATION: (1)..(16)
<223> OTHER INFORMATION: *indicates phosphorothioate modification in
      T*C*G*TCGTTCTCGT*C*G*T

<400> SEQUENCE: 30
tcgtcgttct cgtcgt                                                        16

<210> SEQ ID NO 31
<211> LENGTH: 22
<212> TYPE: DNA
<213> ORGANISM: Artificial Sequence
<220> FEATURE:
<223> OTHER INFORMATION: IDX-9153
<220> FEATURE:
<221> NAME/KEY: misc_feature
<222> LOCATION: (1)..(22)
<223> OTHER INFORMATION: *indicates phosphorothioate modification in
      A*A*C*GACGATGGCAGAACGA*C*G*A

<400> SEQUENCE: 31
aacgacgatg gcagaacgac ga                                                 22

<210> SEQ ID NO 32
<211> LENGTH: 22
<212> TYPE: DNA
<213> ORGANISM: Artificial Sequence
<220> FEATURE:
<223> OTHER INFORMATION: IDX-9146
<220> FEATURE:
<221> NAME/KEY: misc_feature
<222> LOCATION: (1)..(22)
<223> OTHER INFORMATION: *indicates phosphorothioate modification in
      A*A*G*CAGCATGGCAGAAGCA*G*C*A

<400> SEQUENCE: 32
aagcagcatg gcagaagcag ca                                                 22

<210> SEQ ID NO 33
<211> LENGTH: 21
<212> TYPE: DNA
<213> ORGANISM: Artificial Sequence
<220> FEATURE:
<223> OTHER INFORMATION: IDX-9147
<220> FEATURE:
<221> NAME/KEY: misc_feature
<222> LOCATION: (1)..(21)
<223> OTHER INFORMATION: *indicates phosphorothioate modification in
      T*C*G*TCGTTCGTCGTTCGT*C*G*T

<400> SEQUENCE: 33
tcgtcgttcg tcgttcgtcg t                                                  21

<210> SEQ ID NO 34
<211> LENGTH: 21
<212> TYPE: DNA
<213> ORGANISM: Artificial Sequence
<220> FEATURE:
<223> OTHER INFORMATION: IDX-9148
<220> FEATURE:
<221> NAME/KEY: misc_feature
<222> LOCATION: (1)..(21)
<223> OTHER INFORMATION: *indicates phosphorothioate modification in
      T*T*C*TCGTTCTGCCATCGT*G*A*T

<400> SEQUENCE: 34
ttctcgttct gccatcgtga t                                                  21
```

```
<210> SEQ ID NO 35
<211> LENGTH: 16
<212> TYPE: DNA
<213> ORGANISM: Artificial Sequence
<220> FEATURE:
<223> OTHER INFORMATION: IDX-9149
<220> FEATURE:
<221> NAME/KEY: misc_feature
<222> LOCATION: (1)..(16)
<223> OTHER INFORMATION: *indicates phosphorothioate modification in
      T*C*G*TTCCGCCGAT*C*G*T

<400> SEQUENCE: 35
tcgttccgcc gatcgt                                                    16

<210> SEQ ID NO 36
<211> LENGTH: 23
<212> TYPE: DNA
<213> ORGANISM: Artificial Sequence
<220> FEATURE:
<223> OTHER INFORMATION: IDX-9150
<220> FEATURE:
<221> NAME/KEY: misc_feature
<222> LOCATION: (1)..(23)
<223> OTHER INFORMATION: *indicates phosphorothioate modification in
      T*C*G*TCGTTCTGCCATTCGTC*C*A*T

<400> SEQUENCE: 36
tcgtcgttct gccattcgtc cat                                            23

<210> SEQ ID NO 37
<211> LENGTH: 23
<212> TYPE: DNA
<213> ORGANISM: Artificial Sequence
<220> FEATURE:
<223> OTHER INFORMATION: IDX-9151
<220> FEATURE:
<221> NAME/KEY: misc_feature
<222> LOCATION: (1)..(23)
<223> OTHER INFORMATION: *indicates phosphorothioate modification in
      T*C*G*TCCATTCTGCCATCGTC*G*T*T

<400> SEQUENCE: 37
tcgtccattc tgccatcgtc gtt                                            23

<210> SEQ ID NO 38
<211> LENGTH: 22
<212> TYPE: DNA
<213> ORGANISM: Artificial Sequence
<220> FEATURE:
<223> OTHER INFORMATION: IDX-9152
<220> FEATURE:
<221> NAME/KEY: misc_feature
<222> LOCATION: (1)..(22)
<223> OTHER INFORMATION: *indicates phosphorothioate modification in
      T*C*G*TCGTTCTGAAGTCGTC*G*T*T

<400> SEQUENCE: 38
tcgtcgttct gaagtcgtcg tt                                             22

<210> SEQ ID NO 39
<211> LENGTH: 6
<212> TYPE: DNA
<213> ORGANISM: Artificial Sequence
<220> FEATURE:
<223> OTHER INFORMATION: IDX-0491
<220> FEATURE:
<221> NAME/KEY: misc_feature
<222> LOCATION: (1)..(6)
```

```
<223> OTHER INFORMATION: *indicates phosphorothioate modification in
      T*G*G*G*G*T

<400> SEQUENCE: 39 tggggt                                                                      6

<210> SEQ ID NO 40
<211> LENGTH: 11
<212> TYPE: DNA
<213> ORGANISM: Artificial Sequence
<220> FEATURE:
<223> OTHER INFORMATION: IDX-0492
<220> FEATURE:
<221> NAME/KEY: misc_feature
<222> LOCATION: (1)..(11)
<223> OTHER INFORMATION: *indicates phosphorothioate modification in
      G*C*G*GTTTG*C*G*G

<400> SEQUENCE: 40
gcggtttgcg g                                                               11

<210> SEQ ID NO 41
<211> LENGTH: 15
<212> TYPE: DNA
<213> ORGANISM: Artificial Sequence
<220> FEATURE:
<223> OTHER INFORMATION: IDX-0493
<220> FEATURE:
<221> NAME/KEY: misc_feature
<222> LOCATION: (1)..(15)
<223> OTHER INFORMATION: *indicates phosphorothioate modification in
      G*G*T*TGGTGTGGT*T*G*G

<400> SEQUENCE: 41
ggttggtgtg gttgg                                                           15

<210> SEQ ID NO 42
<211> LENGTH: 7
<212> TYPE: DNA
<213> ORGANISM: Artificial Sequence
<220> FEATURE:
<223> OTHER INFORMATION: IDX-0494
<220> FEATURE:
<221> NAME/KEY: misc_feature
<222> LOCATION: (1)..(7)
<223> OTHER INFORMATION: *indicates phosphorothioate modification in
      G*C*A*T*G*C*T

<400> SEQUENCE: 42 gcatgct                                                                     7

<210> SEQ ID NO 43
<211> LENGTH: 24
<212> TYPE: DNA
<213> ORGANISM: Artificial Sequence
<220> FEATURE:
<223> OTHER INFORMATION: IDX-0495
<220> FEATURE:
<221> NAME/KEY: misc_feature
<222> LOCATION: (1)..(24)
<223> OTHER INFORMATION: *indicates phosphorothioate modification in
      G*C*C*TACTAAGTAATGACTGTC*A*T*G

<400> SEQUENCE: 43
gcctactaag taatgactgt catg                                                 24

<210> SEQ ID NO 44
<211> LENGTH: 22
<212> TYPE: DNA
```

```
<213> ORGANISM: Artificial Sequence
<220> FEATURE:
<223> OTHER INFORMATION: IDX-9022
<220> FEATURE:
<221> NAME/KEY: misc_feature
<222> LOCATION: (1)..(22)
<223> OTHER INFORMATION: *indicates phosphorothioate modification in
      T*C*G*TCGTTCTGCCATCGTC*G*T*T

<400> SEQUENCE: 44
tcgtcgttct gccatcgtcg tt                                             22

<210> SEQ ID NO 45
<211> LENGTH: 27
<212> TYPE: DNA
<213> ORGANISM: Artificial Sequence
<220> FEATURE:
<223> OTHER INFORMATION: IDX-9012
<220> FEATURE:
<221> NAME/KEY: misc_feature
<222> LOCATION: (1)..(27)
<223> OTHER INFORMATION: *indicates phosphorothioate modification in
      T*C*G*TTCGTCTTGTTCGTCTTGTTC*G*T*C

<400> SEQUENCE: 45
tcgttcgtct tgttcgtctt gttcgtc                                        27

<210> SEQ ID NO 46
<211> LENGTH: 18
<212> TYPE: DNA
<213> ORGANISM: Artificial Sequence
<220> FEATURE:
<223> OTHER INFORMATION: IDX-9010
<220> FEATURE:
<221> NAME/KEY: misc_feature
<222> LOCATION: (1)..(18)
<223> OTHER INFORMATION: *indicates phosphorothioate modification in
      T*C*C*CAAGAGTCGTCC*A*G*G

<400> SEQUENCE: 46
tcccaagagt cgtccagg                                                  18

<210> SEQ ID NO 47
<211> LENGTH: 21
<212> TYPE: DNA
<213> ORGANISM: Artificial Sequence
<220> FEATURE:
<223> OTHER INFORMATION: IDX-9071
<220> FEATURE:
<221> NAME/KEY: misc_feature
<222> LOCATION: (1)..(21)
<223> OTHER INFORMATION: *indicates phosphorothioate modification in
      T*C*G*TTCGTCTGCTTGTTC*G*T*C

<400> SEQUENCE: 47
tcgttcgtct gcttgttcgt c                                              21

<210> SEQ ID NO 48
<211> LENGTH: 24
<212> TYPE: DNA
<213> ORGANISM: Artificial Sequence
<220> FEATURE:
<223> OTHER INFORMATION: IDX-0001
<220> FEATURE:
<221> NAME/KEY: misc_feature
<222> LOCATION: (1)..(24)
<223> OTHER INFORMATION: *indicates phosphorothioate modification in
      T*C*C*GCGTTCGGCCTCCTGGCG*C*G*G

<400> SEQUENCE: 48
```
tccgcgttcg gcctcctggc gcgg                                           24

<210> SEQ ID NO 49
<211> LENGTH: 23
<212> TYPE: DNA
<213> ORGANISM: Artificial Sequence
<220> FEATURE:
<223> OTHER INFORMATION: IDX-9024
<220> FEATURE:
<221> NAME/KEY: misc_feature
<222> LOCATION: (1)..(23)
<223> OTHER INFORMATION: *indicates phosphorothioate modification in
      T*G*C*CATTCGTCGTTCTCGTC*G*T*T

<400> SEQUENCE: 49
tgccattcgt cgttctcgtc gtt                                            23

<210> SEQ ID NO 50
<211> LENGTH: 21
<212> TYPE: DNA
<213> ORGANISM: Artificial Sequence
<220> FEATURE:
<223> OTHER INFORMATION: IDX-9038
<220> FEATURE:
<221> NAME/KEY: misc_feature
<222> LOCATION: (1)..(21)
<223> OTHER INFORMATION: *indicates phosphorothioate modification in
      T*C*G*TCGTTCGGCCGATCG*T*C*C

<400> SEQUENCE: 50
tcgtcgttcg gccgatcgtc c                                              21

<210> SEQ ID NO 51
<211> LENGTH: 19
<212> TYPE: DNA
<213> ORGANISM: Artificial Sequence
<220> FEATURE:
<223> OTHER INFORMATION: IDX-9074
<220> FEATURE:
<221> NAME/KEY: misc_feature
<222> LOCATION: (1)..(19)
<223> OTHER INFORMATION: *indicates phosphorothioate modification in
      T*C*G*TTCGTCTTTCGTC*T*G*C

<400> SEQUENCE: 51
tcgttcgtct ttcgtctgc                                                 19

<210> SEQ ID NO 52
<211> LENGTH: 22
<212> TYPE: DNA
<213> ORGANISM: Artificial Sequence
<220> FEATURE:
<223> OTHER INFORMATION: IDX-9087
<220> FEATURE:
<221> NAME/KEY: misc_feature
<222> LOCATION: (1)..(22)
<223> OTHER INFORMATION: *indicates phosphorothioate modification in
      T*C*G*TCTGCTTAGTTCGTTA*G*T*T

<400> SEQUENCE: 52
tcgtctgctt agttcgttag tt                                             22

<210> SEQ ID NO 53
<211> LENGTH: 23
<212> TYPE: DNA
<213> ORGANISM: Artificial Sequence
<220> FEATURE:
<223> OTHER INFORMATION: IDX-9092
<220> FEATURE:
<221> NAME/KEY: misc_feature

```
<222> LOCATION: (1)..(23)
<223> OTHER INFORMATION: *indicates phosphorothioate modification in
      T*T*T*CGTCTGCTTTCGTTTCG*T*T*T

<400> SEQUENCE: 53
tttcgtctgc tttcgtttcg ttt                                            23

<210> SEQ ID NO 54
<211> LENGTH: 18
<212> TYPE: DNA
<213> ORGANISM: Artificial Sequence
<220> FEATURE:
<223> OTHER INFORMATION: IDX-9095
<220> FEATURE:
<221> NAME/KEY: misc_feature
<222> LOCATION: (1)..(18)
<223> OTHER INFORMATION: *indicates phosphorothioate modification in
      T*C*G*TCTGCTTTCGTC*T*G*C

<400> SEQUENCE: 54
tcgtctgctt tcgtctgc                                                  18

<210> SEQ ID NO 55
<211> LENGTH: 16
<212> TYPE: DNA
<213> ORGANISM: Artificial Sequence
<220> FEATURE:
<223> OTHER INFORMATION: IDX-9096
<220> FEATURE:
<221> NAME/KEY: misc_feature
<222> LOCATION: (1)..(16)
<223> OTHER INFORMATION: *indicates phosphorothioate modification in
      G*A*T*CGTCCGATCG*T*C*C

<400> SEQUENCE: 55
gatcgtccga tcgtcc                                                    16

<210> SEQ ID NO 56
<211> LENGTH: 24
<212> TYPE: DNA
<213> ORGANISM: Artificial Sequence
<220> FEATURE:
<223> OTHER INFORMATION: IDX-0910
<220> FEATURE:
<221> NAME/KEY: misc_feature
<222> LOCATION: (1)..(24)
<223> OTHER INFORMATION: *indicates phosphorothioate modification in
      T*C*G*T*C*G*T*T*T*T*G*T*C*G*T*T*T*T*G*T*C*G*T*T

<400> SEQUENCE: 56
tcgtcgtttt gtcgttttgt cgtt                                           24

<210> SEQ ID NO 57
<211> LENGTH: 24
<212> TYPE: DNA
<213> ORGANISM: Artificial Sequence
<220> FEATURE:
<223> OTHER INFORMATION: IDX-0912
<220> FEATURE:
<221> NAME/KEY: misc_feature
<222> LOCATION: (1)..(24)
<223> OTHER INFORMATION: *indicates phosphorothioate modification in
      T*C*G*TCGTTTTGTCGTTTTGTC*G*T*T

<400> SEQUENCE: 57
tcgtcgtttt gtcgttttgt cgtt                                           24

<210> SEQ ID NO 58
<211> LENGTH: 21
```

```
<212> TYPE: DNA
<213> ORGANISM: Artificial Sequence
<220> FEATURE:
<223> OTHER INFORMATION: IDX-9009
<220> FEATURE:
<221> NAME/KEY: misc_feature
<222> LOCATION: (1)..(21)
<223> OTHER INFORMATION: *indicates phosphorothioate modification in
      T*G*C*GCGCGGCCTCTCCTC*G*C*C

<400> SEQUENCE: 58
tgcgcgcggc ctctcctcgc c                                              21

<210> SEQ ID NO 59
<211> LENGTH: 15
<212> TYPE: DNA
<213> ORGANISM: Artificial Sequence
<220> FEATURE:
<223> OTHER INFORMATION: IDX-0465
<220> FEATURE:
<221> NAME/KEY: misc_feature
<222> LOCATION: (1)..(15)
<223> OTHER INFORMATION: *indicates phosphorothioate modification in
      G*G*G*GTGCTCTGC*G*G*G

<400> SEQUENCE: 59
ggggtgctct gcggg                                                     15

<210> SEQ ID NO 60
<211> LENGTH: 21
<212> TYPE: DNA
<213> ORGANISM: Artificial Sequence
<220> FEATURE:
<223> OTHER INFORMATION: IDX-9008
<220> FEATURE:
<221> NAME/KEY: misc_feature
<222> LOCATION: (1)..(21)
<223> OTHER INFORMATION: *indicates phosphorothioate modification in
      T*C*T*GTCGTGTCCTTCTTT*G*G*C

<400> SEQUENCE: 60
tctgtcgtgt ccttctttgg c                                              21

<210> SEQ ID NO 61
<211> LENGTH: 24
<212> TYPE: DNA
<213> ORGANISM: Artificial Sequence
<220> FEATURE:
<223> OTHER INFORMATION: IDX-9018
<220> FEATURE:
<221> NAME/KEY: misc_feature
<222> LOCATION: (1)..(24)
<223> OTHER INFORMATION: *indicates phosphorothioate modification in
      T*C*G*TCGTCTGAAGCCGCGCGC*G*G*C

<400> SEQUENCE: 61
tcgtcgtctg aagccgcgcg cggc                                           24

<210> SEQ ID NO 62
<211> LENGTH: 20
<212> TYPE: DNA
<213> ORGANISM: Artificial Sequence
<220> FEATURE:
<223> OTHER INFORMATION: IDX-9019
<220> FEATURE:
<221> NAME/KEY: misc_feature
<222> LOCATION: (1)..(20)
<223> OTHER INFORMATION: *indicates phosphorothioate modification in
      T*C*G*TCGTCTGAAGCCGC*G*G*C

<400> SEQUENCE: 62
```
tcgtcgtctg aagccgcggc                                              20

<210> SEQ ID NO 63
<211> LENGTH: 23
<212> TYPE: DNA
<213> ORGANISM: Artificial Sequence
<220> FEATURE:
<223> OTHER INFORMATION: IDX-9020
<220> FEATURE:
<221> NAME/KEY: misc_feature
<222> LOCATION: (1)..(23)
<223> OTHER INFORMATION: *indicates phosphorothioate modification in
      C*T*G*AAGCCGCGGCTTTCGTC*G*T*T

<400> SEQUENCE: 63
ctgaagccgc ggctttcgtc gtt                                          23

<210> SEQ ID NO 64
<211> LENGTH: 20
<212> TYPE: DNA
<213> ORGANISM: Artificial Sequence
<220> FEATURE:
<223> OTHER INFORMATION: IDX-9021
<220> FEATURE:
<221> NAME/KEY: misc_feature
<222> LOCATION: (1)..(20)
<223> OTHER INFORMATION: *indicates phosphorothioate modification in
      C*T*G*AAGCCGGCTTCGTC*G*T*T

<400> SEQUENCE: 64
ctgaagccgg cttcgtcgtt                                              20

<210> SEQ ID NO 65
<211> LENGTH: 23
<212> TYPE: DNA
<213> ORGANISM: Artificial Sequence
<220> FEATURE:
<223> OTHER INFORMATION: IDX-9023
<220> FEATURE:
<221> NAME/KEY: misc_feature
<222> LOCATION: (1)..(23)
<223> OTHER INFORMATION: *indicates phosphorothioate modification in
      T*C*G*TCGATTCTGAAGTCGTC*G*T*T

<400> SEQUENCE: 65
tcgtcgattc tgaagtcgtc gtt                                          23

<210> SEQ ID NO 66
<211> LENGTH: 22
<212> TYPE: DNA
<213> ORGANISM: Artificial Sequence
<220> FEATURE:
<223> OTHER INFORMATION: IDX-9026
<220> FEATURE:
<221> NAME/KEY: misc_feature
<222> LOCATION: (1)..(22)
<223> OTHER INFORMATION: *indicates phosphorothioate modification in
      G*T*T*CGTCGATGGCCGGCCG*G*C*C

<400> SEQUENCE: 66
gttcgtcgat ggccggccgg cc                                           22

<210> SEQ ID NO 67
<211> LENGTH: 17
<212> TYPE: DNA
<213> ORGANISM: Artificial Sequence
<220> FEATURE:
<223> OTHER INFORMATION: IDX-9027
<220> FEATURE:

```
<221> NAME/KEY: misc_feature
<222> LOCATION: (1)..(17)
<223> OTHER INFORMATION: *indicates phosphorothioate modification in
      T*T*C*GTCGATGGCCG*G*C*C

<400> SEQUENCE: 67
ttcgtcgatg gccggcc                                              17

<210> SEQ ID NO 68
<211> LENGTH: 23
<212> TYPE: DNA
<213> ORGANISM: Artificial Sequence
<220> FEATURE:
<223> OTHER INFORMATION: IDX-9039
<220> FEATURE:
<221> NAME/KEY: misc_feature
<222> LOCATION: (1)..(23)
<223> OTHER INFORMATION: *indicates phosphorothioate modification in
      G*G*G*GTCGTCTGCTATCGATG*G*G*G

<400> SEQUENCE: 68
ggggtcgtct gctatcgatg ggg                                       23

<210> SEQ ID NO 69
<211> LENGTH: 23
<212> TYPE: DNA
<213> ORGANISM: Artificial Sequence
<220> FEATURE:
<223> OTHER INFORMATION: IDX-9040
<220> FEATURE:
<221> NAME/KEY: misc_feature
<222> LOCATION: (1)..(23)
<223> OTHER INFORMATION: *indicates phosphorothioate modification in
      G*G*G*GTCGTCTGCGATCGATG*G*G*G

<400> SEQUENCE: 69
ggggtcgtct gcgatcgatg ggg                                       23

<210> SEQ ID NO 70
<211> LENGTH: 24
<212> TYPE: DNA
<213> ORGANISM: Artificial Sequence
<220> FEATURE:
<223> OTHER INFORMATION: IDX-9041
<220> FEATURE:
<221> NAME/KEY: misc_feature
<222> LOCATION: (1)..(24)
<223> OTHER INFORMATION: *indicates phosphorothioate modification in
      G*G*T*CGTCTGCGACGATCGTCG*G*G*G

<400> SEQUENCE: 70
ggtcgtctgc gacgatcgtc gggg                                      24

<210> SEQ ID NO 71
<211> LENGTH: 24
<212> TYPE: DNA
<213> ORGANISM: Artificial Sequence
<220> FEATURE:
<223> OTHER INFORMATION: IDX-9042
<220> FEATURE:
<221> NAME/KEY: misc_feature
<222> LOCATION: (1)..(24)
<223> OTHER INFORMATION: *indicates phosphorothioate modification in
      C*C*T*CGTCTGCGACGATCGTCG*G*G*G

<400> SEQUENCE: 71
cctcgtctgc gacgatcgtc gggg                                      24

<210> SEQ ID NO 72
```

-continued

```
<211> LENGTH: 16
<212> TYPE: DNA
<213> ORGANISM: Artificial Sequence
<220> FEATURE:
<223> OTHER INFORMATION: IDX-9047
<220> FEATURE:
<221> NAME/KEY: misc_feature
<222> LOCATION: (1)..(16)
<223> OTHER INFORMATION: *indicates phosphorothioate modification in
      G*G*G*GTCGTCTGCT*G*G*G

<400> SEQUENCE: 72
ggggtcgtct gctggg                                                       16

<210> SEQ ID NO 73
<211> LENGTH: 16
<212> TYPE: DNA
<213> ORGANISM: Artificial Sequence
<220> FEATURE:
<223> OTHER INFORMATION: IDX-9048
<220> FEATURE:
<221> NAME/KEY: misc_feature
<222> LOCATION: (1)..(16)
<223> OTHER INFORMATION: *indicates phosphorothioate modification in
      G*G*G*GTCGTCTGCG*G*G*G

<400> SEQUENCE: 73
ggggtcgtct gcgggg                                                       16

<210> SEQ ID NO 74
<211> LENGTH: 17
<212> TYPE: DNA
<213> ORGANISM: Artificial Sequence
<220> FEATURE:
<223> OTHER INFORMATION: IDX-9049
<220> FEATURE:
<221> NAME/KEY: misc_feature
<222> LOCATION: (1)..(17)
<223> OTHER INFORMATION: *indicates phosphorothioate modification in
      G*G*G*GTCGTCTGCTC*G*G*G

<400> SEQUENCE: 74
ggggtcgtct gctcggg                                                      17

<210> SEQ ID NO 75
<211> LENGTH: 17
<212> TYPE: DNA
<213> ORGANISM: Artificial Sequence
<220> FEATURE:
<223> OTHER INFORMATION: IDX-9050
<220> FEATURE:
<221> NAME/KEY: misc_feature
<222> LOCATION: (1)..(17)
<223> OTHER INFORMATION: *indicates phosphorothioate modification in
      G*G*G*GTCGTCTGCCA*G*G*G

<400> SEQUENCE: 75
ggggtcgtct gccaggg                                                      17

<210> SEQ ID NO 76
<211> LENGTH: 20
<212> TYPE: DNA
<213> ORGANISM: Artificial Sequence
<220> FEATURE:
<223> OTHER INFORMATION: IDX-9055
<220> FEATURE:
<221> NAME/KEY: misc_feature
<222> LOCATION: (1)..(20)
<223> OTHER INFORMATION: *indicates phosphorothioate modification in
      G*A*T*CGTCCGGGTCCCGG*G*G*G
```

<400> SEQUENCE: 76
gatcgtccgg gtcccggggg                                              20

<210> SEQ ID NO 77
<211> LENGTH: 15
<212> TYPE: DNA
<213> ORGANISM: Artificial Sequence
<220> FEATURE:
<223> OTHER INFORMATION: IDX-9057
<220> FEATURE:
<221> NAME/KEY: misc_feature
<222> LOCATION: (1)..(15)
<223> OTHER INFORMATION: *indicates phosphorothioate modification in
      G*A*T*CGTCCGCGG*G*G*G

<400> SEQUENCE: 77
gatcgtccgc ggggg                                                   15

<210> SEQ ID NO 78
<211> LENGTH: 21
<212> TYPE: DNA
<213> ORGANISM: Artificial Sequence
<220> FEATURE:
<223> OTHER INFORMATION: IDX-9067
<220> FEATURE:
<221> NAME/KEY: misc_feature
<222> LOCATION: (1)..(21)
<223> OTHER INFORMATION: *indicates phosphorothioate modification in
      T*C*G*T*C*T*G*C*C*A*T*G*G*C*G*G*C*C*G*C*C

<400> SEQUENCE: 78
tcgtctgcca tggcggccgc c                                            21

<210> SEQ ID NO 79
<211> LENGTH: 21
<212> TYPE: DNA
<213> ORGANISM: Artificial Sequence
<220> FEATURE:
<223> OTHER INFORMATION: IDX-9068
<220> FEATURE:
<221> NAME/KEY: misc_feature
<222> LOCATION: (1)..(21)
<223> OTHER INFORMATION: *indicates phosphorothioate modification in
      T*C*G*TCTGCCATGGCGCGC*C*G*G

<400> SEQUENCE: 79
tcgtctgcca tggcgcgccg g                                            21

<210> SEQ ID NO 80
<211> LENGTH: 12
<212> TYPE: DNA
<213> ORGANISM: Artificial Sequence
<220> FEATURE:
<223> OTHER INFORMATION: IDX-9133
<220> FEATURE:
<221> NAME/KEY: misc_feature
<222> LOCATION: (1)..(12)
<223> OTHER INFORMATION: *indicates phosphorothioate modification in
      G*A*T*CGTCCG*T*G*T

<400> SEQUENCE: 80
gatcgtccgt gt                                                      12

<210> SEQ ID NO 81
<211> LENGTH: 15
<212> TYPE: DNA
<213> ORGANISM: Artificial Sequence
<220> FEATURE:
<223> OTHER INFORMATION: IDX-9054

```
<220> FEATURE:
<221> NAME/KEY: misc_feature
<222> LOCATION: (1)..(15)
<223> OTHER INFORMATION: *indicates phosphorothioate modification in
      G*G*G*GTCGTCTGC*G*G*G

<400> SEQUENCE: 81
ggggtcgtct gcggg                                                      15

<210> SEQ ID NO 82
<211> LENGTH: 15
<212> TYPE: DNA
<213> ORGANISM: Artificial Sequence
<220> FEATURE:
<223> OTHER INFORMATION: IDX-0440

<400> SEQUENCE: 82
ggggtcgtct gcggg                                                      15

<210> SEQ ID NO 83
<211> LENGTH: 12
<212> TYPE: DNA
<213> ORGANISM: Artificial Sequence
<220> FEATURE:
<223> OTHER INFORMATION: IDX-9059
<220> FEATURE:
<221> NAME/KEY: misc_feature
<222> LOCATION: (1)..(12)
<223> OTHER INFORMATION: *indicates phosphorothioate modification in
      G*A*T*CGTCCG*G*G*G

<400> SEQUENCE: 83
gatcgtccgg gg                                                         12

<210> SEQ ID NO 84
<211> LENGTH: 15
<212> TYPE: DNA
<213> ORGANISM: Artificial Sequence
<220> FEATURE:
<223> OTHER INFORMATION: IDX-9004
<220> FEATURE:
<221> NAME/KEY: misc_feature
<222> LOCATION: (1)..(15)
<223> OTHER INFORMATION: *indicates phosphorothioate modification in
      G*G*G*GTCGCAGCT*G*G*G

<400> SEQUENCE: 84
ggggtcgcag ctggg                                                      15

<210> SEQ ID NO 85
<211> LENGTH: 25
<212> TYPE: DNA
<213> ORGANISM: Artificial Sequence
<220> FEATURE:
<223> OTHER INFORMATION: IDX-9005
<220> FEATURE:
<221> NAME/KEY: misc_feature
<222> LOCATION: (1)..(25)
<223> OTHER INFORMATION: *indicates phosphorothioate modification in
      T*C*G*TCCATGGTCAGGGTCCCGG*G*G*G

<400> SEQUENCE: 85
tcgtccatgg tcagggtccc ggggg                                           25

<210> SEQ ID NO 86
<211> LENGTH: 21
<212> TYPE: DNA
<213> ORGANISM: Artificial Sequence
<220> FEATURE:
```

<223> OTHER INFORMATION: IDX-9030
<220> FEATURE:
<221> NAME/KEY: misc_feature
<222> LOCATION: (1)..(21)
<223> OTHER INFORMATION: *indicates phosphorothioate modification in
    T*C*G*TCTGCCATGGCGGCC*G*C*C

<400> SEQUENCE: 86
tcgtctgcca tggcggccgc c                                              21

<210> SEQ ID NO 87
<211> LENGTH: 15
<212> TYPE: DNA
<213> ORGANISM: Artificial Sequence
<220> FEATURE:
<223> OTHER INFORMATION: IDX-9060
<220> FEATURE:
<221> NAME/KEY: misc_feature
<222> LOCATION: (1)..(15)
<223> OTHER INFORMATION: *indicates phosphorothioate modification in
    G*G*G*GATCGTCCG*G*G*G

<400> SEQUENCE: 87
ggggatcgtc cgggg                                                     15

<210> SEQ ID NO 88
<211> LENGTH: 13
<212> TYPE: DNA
<213> ORGANISM: Artificial Sequence
<220> FEATURE:
<223> OTHER INFORMATION: IDX-9045
<220> FEATURE:
<221> NAME/KEY: misc_feature
<222> LOCATION: (1)..(13)
<223> OTHER INFORMATION: *indicates phosphorothioate modification in
    G*G*G*TCGCAGC*T*G*G

<400> SEQUENCE: 88
gggtcgcagc tgg                                                       13

<210> SEQ ID NO 89
<211> LENGTH: 13
<212> TYPE: DNA
<213> ORGANISM: Artificial Sequence
<220> FEATURE:
<223> OTHER INFORMATION: IDX-9053
<220> FEATURE:
<221> NAME/KEY: misc_feature
<222> LOCATION: (1)..(13)
<223> OTHER INFORMATION: *indicates phosphorothioate modification in
    G*G*G*TCGTCTG*C*G*G

<400> SEQUENCE: 89
gggtcgtctg cgg                                                       13

<210> SEQ ID NO 90
<211> LENGTH: 16
<212> TYPE: DNA
<213> ORGANISM: Artificial Sequence
<220> FEATURE:
<223> OTHER INFORMATION: IDX-9058
<220> FEATURE:
<221> NAME/KEY: misc_feature
<222> LOCATION: (1)..(16)
<223> OTHER INFORMATION: *indicates phosphorothioate modification in
    G*A*T*CGTCCGTCGG*G*G*G

<400> SEQUENCE: 90
gatcgtccgt cggggg                                                    16

```
<210> SEQ ID NO 91
<211> LENGTH: 15
<212> TYPE: DNA
<213> ORGANISM: Artificial Sequence
<220> FEATURE:
<223> OTHER INFORMATION: IDX-0445
<220> FEATURE:
<221> NAME/KEY: misc_feature
<222> LOCATION: (1)..(15)
<223> OTHER INFORMATION: *indicates phosphorothioate modification in
      G*G*G*G*T*C*G*T*C*T*G*C*G*G*G

<400> SEQUENCE: 91
ggggtcgtct gcggg                                                  15

<210> SEQ ID NO 92
<211> LENGTH: 15
<212> TYPE: DNA
<213> ORGANISM: Artificial Sequence
<220> FEATURE:
<223> OTHER INFORMATION: IDX-0455
<220> FEATURE:
<221> NAME/KEY: misc_feature
<222> LOCATION: (1)..(15)
<223> OTHER INFORMATION: *indicates phosphorothioate modification in
      G*G*G*GCCGTCTGC*G*G*G

<400> SEQUENCE: 92
ggggccgtct gcggg                                                  15

<210> SEQ ID NO 93
<211> LENGTH: 15
<212> TYPE: DNA
<213> ORGANISM: Artificial Sequence
<220> FEATURE:
<223> OTHER INFORMATION: IDX-0460
<220> FEATURE:
<221> NAME/KEY: misc_feature
<222> LOCATION: (1)..(15)
<223> OTHER INFORMATION: *indicates phosphorothioate modification in
      G*G*G*CCCGTCTGC*G*G*G

<400> SEQUENCE: 93
gggcccgtct gcggg                                                  15

<210> SEQ ID NO 94
<211> LENGTH: 12
<212> TYPE: DNA
<213> ORGANISM: Artificial Sequence
<220> FEATURE:
<223> OTHER INFORMATION: IDX-9134
<220> FEATURE:
<221> NAME/KEY: misc_feature
<222> LOCATION: (1)..(12)
<223> OTHER INFORMATION: *indicates phosphorothioate modification in
      G*A*T*GCTCTG*G*G*G

<400> SEQUENCE: 94
gatgctctgg gg                                                     12
```